(12) United States Patent
Merce Vidal et al.

(10) Patent No.: US 7,462,640 B2
(45) Date of Patent: Dec. 9, 2008

(54) INDOL-6YL SULFONAMIDE DERIVATIVES, THEIR PREPARATION AND THEIR USE AS 5-HT-6 AS MODULATORS

(75) Inventors: Ramon Merce Vidal, Barcelona (ES); Xavier Codony Soler, Mataro (ES); Alberto Dordal Zueras, Barcelona (ES)

(73) Assignee: Laboratorios del Dr. Esteve S.A., Barcelona (ES)

( * ) Notice: Subject to any disclaimer, the term of this patent is extended or adjusted under 35 U.S.C. 154(b) by 0 days.

(21) Appl. No.: 10/566,101

(22) PCT Filed: Jul. 29, 2004

(86) PCT No.: PCT/EP2004/008510

§ 371 (c)(1),
(2), (4) Date: Aug. 10, 2006

(87) PCT Pub. No.: WO2005/013976

PCT Pub. Date: Feb. 17, 2005

(65) Prior Publication Data

US 2007/0043041 A1    Feb. 22, 2007

(30) Foreign Application Priority Data

Jul. 30, 2003    (ES)    ............................... 200301810

(51) Int. Cl.
*A01N 43/38* (2006.01)
*A61K 31/405* (2006.01)
*C07D 209/04* (2006.01)

(52) U.S. Cl. .................. 514/415; 548/490; 548/491

(58) Field of Classification Search ................. 548/490, 548/491; 514/415
See application file for complete search history.

(56) References Cited

U.S. PATENT DOCUMENTS

| 3,472,870 A | 10/1969 | Larsen et al. |
| 2003/0191124 A1 | 10/2003 | Merce-Vidal et al. |
| 2005/0032791 A1 | 2/2005 | Merce-Vidal et al. |
| 2005/0065202 A1 | 3/2005 | Vidal et al. |
| 2007/0043041 A1 | 2/2007 | Vidal et al. |

FOREIGN PATENT DOCUMENTS

| EP | 0 733 628 A1 | 6/1996 |
| EP | 0 815 861 | 1/1998 |
| EP | 0 815 961 | 1/1998 |
| WO | WO 95/32967 | 12/1995 |
| WO | WO 01/32646 A2 | 5/2001 |
| WO | 02/060871 | 8/2002 |
| WO | WO 02/066470 A1 | 8/2002 |
| WO | 03/042175 | 5/2003 |

OTHER PUBLICATIONS

Liu et al., Psychiatry and clinical neurosciences, 2001, vol. 55, pp. 427-429.*
Laconde et al., Journal of enzyme inhibition and medicinal chemistry, 2003, vol. 18, pp. 89-94.*
D. Hoyer, et al., Neuropharmacology, vol. 36, No. 4/5, pp. 419-428 (1997).
F.J. Monsma, Jr., et al., Molecular Pharmacology, vol. 43, pp. 320-327 (1993).
M. Ruat, et al., Biochemical and Biophysical Research Communications, vol. 193, No. 1, pp. 268-276 (1993).
R. Kohen, et al., Journal of Neurochemistry, vol. 66, No. 1, pp. 47-56 (1996).
M. Yoshioka, et al., Ann. NY Acad. Sci. vol. 861, pp. 244 (1998).
A.V. Turnbull, et al., Diabetes, vol. 51, pp. 2441-2449 (2002).
A. Bourson, et al., British jurnal of Pharmacology, vol. 125, pp. 1562-1566 (1998).
D.C. Rogers, et al., Br. J. Pharmacol. Supp., vol. 127, pp. 22P (1999).
A. Bourson, et al., J. Pharmacol. Exp. Ther., vol. 274, No. 1, pp. 173-180 (1995).
A.J. Sleight, et al., Behavioural Brain Research, vol. 73, pp. 245-248 (1996).
T.A. Branchek, et al., Annu. Rev. Pharmacol. Toxicol, vol. 40, pp. 319-334 (2000).
C. Routledge, British Journal of Pharmacology, vol. 130, pp. 1606-1612 (2000).
B.L. Roth, et al., J. Pharmacol. Exp. Ther., vol. 268, pp. 1403-1410 (1994).

(Continued)

*Primary Examiner*—D. Margaret Seaman
*Assistant Examiner*—Niloofar Rahmani
(74) *Attorney, Agent, or Firm*—Oblon, Spivak, McClelland, Maier & Neustadt, P.C.

(57) ABSTRACT

The present invention refers to new sulfonamide derivatives, of general formula (Ia, Ib, Ic) optionally in form of one of their stereoisomers, preferably enantiomers or diastereomers, their racemate, or in form of a mixture of at least two of their stereoisomers, preferably enantiomers or diastereomers, at any mixing ratio or their salts, preferably the corresponding, physiologically acceptable salts, or corresponding solvates; to the process for their preparation, to their application as medicaments in human and/or veterinary therapeutics, and to the pharmaceutical compositions containing them.

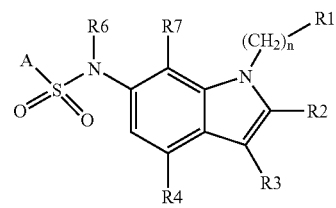

46 Claims, No Drawings

OTHER PUBLICATIONS

C.E. Glatt, et al., Molecular Medicine, vol. 1, No. 4, pp. 398-406 (1995).

T. Shinkai, et al., American Journal of Medical Genetics (Neuropsychiatric Genetics), vol. 88, pp. 120-122 (1999).

C. Gerard, et al., Brain Research, vol. 746, pp. 207-219 (1997).

M.R. Pranzatelli, Drugs of Today, vol. 33, No. 6, pp. 379-392 (1997).

E.E. Gilbert, Synthesis-International Journal of Methods in Synthetic Organic Chemistry No. 1, pp. 3-10 (1969).

L.D. Basanagoudar, et al., J. Indian Chem. Soc., vol. 49, No. 8, pp. 811-813 (1972).

S.A. Yamashkin, et al., Chemistry of Heterocyclic Compounds, vol. 35, No. 12, pp. 1426-1432 (1999).

S.R. Boothroyd, et al., Tetrahedron Letters, vol. 36, No. 14, pp. 2411-2414 (1995).

J.E. Macor, et al., Synthetic Communications, vol. 23, No. 1, pp. 65-72 (1993).

M. Macchia, et al., IL. Farmaco, vol. 51, No. 1, pp. 75-78 (1996).

S.S. Bhagwat, et al., Tetrahedron Letters, vol. 35, No. 12, pp. 1847-1850 (1994).

L.D. Bratton, et al., J. Heterocyclic Chem., vol. 37, pp. 1103-1108 (2000).

O. Ottoni, et al., Tetrahedron Letters, vol. 40, pp. 1117-1120 (1999).

S.L. Vorobeva, et al., Khim Geterosiki Soedin (KGSSAQ) (5), pp. 636-637 (1991).

A.R. Katritzky, et al., Org. Prep. Proceed. Inc. (OPPIAK), vol. 23, No. 3, pp. 357-363 (1991).

N. Moskalev, et al., Heterocycles (HTCYAM), vol. 52, No. 2, pp. 533-536 (2000).

P.J. Munson, et al., Analytical Biochemistry, vol. 107, pp. 220-239 (1980).

A. Kask, et al., European Journal of Pharmacology, vol. 414, pp. 215-224 (2001).

"Oral drug deliver, small intestine and colon", Encyclopedia of Controlled Drug Deliver, Mathiowitz, E. (Ed.), John Wiley & Sons, Inc., New York, vol. 2, 698-728 (1999).

W.D. Hirst, et al., British Journal of Pharmacology, vol 130, pp. 1597-1605 (2000).

M.L. Woolley, et al., Neuropharmacology, vol. 41, pp. 210-219 (2001).

M. Abou-Gharbia, et al., Eur. J. Med. Chem., vol. 23, pp. 373-377 (1988).

K. Yamada, et al., Heterocycles, vol. 55, No. 6, pp. 1151-1159 (2001).

K. Takada, et al., "Oral Drug Delivery", Encyclopedia of Controlled Drug Deliver, Mathiowiz, E., (ed.), John Wiley and Sons, Inc., New York, vol. 2, pp. 728-742 (1999).

Dictionary of Microbiology and Molecular Biology, Second Edition, Paul Singleton/Diana Sainsbury, pp. 707 and 934.

J.C. Bentley, et al., J. Psychopharmacol., p. A64, Abstract No. 255 (1997).

J.C. Bentley, et al., British Journal of Pharmacology, vol. 126, pp. 1537-1542 (1999).

J. Svartengren, et al., Int. J. Obes, p. 566, Abstract No. T1:P1-094 (2003).

Brown, Frederick J. et al: "Evolution of a Series of Peptidoleukotriene Antagonists: Synthesis and Structure-Activity Relationships of 1, 6-Disubstituted Indoles and Indazoles", Journal of Medicinal Chemistry, vol. 6 No. 33, pp. 1771-1781, 1990.

Laconde, G. et al., "New Analogues of the Anticancer E7070: Synthesis and Pharmacology", Journal of Enzyme Inhibition and Medicinal Chemistry, vol. 18, No. 2, pp. 89-94, 2003.

U.S. Appl. No. 11/679,344, filed Feb. 27, 2007, Merce Vidal.

U.S. Appl. No. 11/673,328, filed Feb. 9, 2007, Merce Vidal et al.

* cited by examiner

INDOL-6YL SULFONAMIDE DERIVATIVES, THEIR PREPARATION AND THEIR USE AS 5-HT-6 AS MODULATORS

The present invention relates to new sulfonamide derivatives, of general formula (Ia, Ib, Ic),

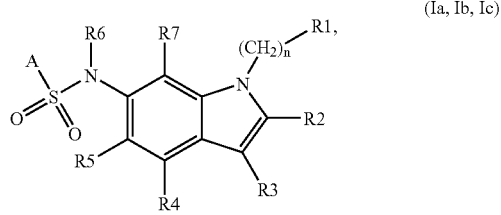

(Ia, Ib, Ic)

optionally in form of one of their stereoisomers, preferably enantiomers or diastereomers, a racemate, or in form of a mixture of at least two of their stereoisomers, preferably enantiomers or diastereomers, in any mixing ratio, or their salts, preferably the corresponding, physiologically acceptable salts, or corresponding solvates; to the processes for their preparation, to their application in medicaments in human and/or veterinary therapeutics, and to pharmaceutical compositions containing them.

The new compounds of the present invention can be used in the pharmaceutical industry as intermediates and for the manufacture of medicaments.

The superfamily of serotonin receptors (5-HT) comprises 7 classes ($5\text{-}HT_1\text{-}5\text{-}HT_7$), which cover 14 human subclasses [D. Hoyer, et al., *Neuropharmacology*, 1997, 36, 419]. The $5\text{-}HT_6$ receptor has been the last serotonin receptor identified by molecular cloning in rats [F. J. Monsma, et al., *Mol. Pharmacol.*, 1993, 43, 320; M. Ruat, et al., *Biochem. Biophys. Res. Commun.*, 1993, 193, 268] as well as in humans [R. Kohen, et al., *J. Neurochem.*, 1996, 66, 47]. The compounds with an affinity for the $5\text{-}HT_6$ receptor are useful in treating different disorders of the Central Nervous System and of the Gastrointestinal system, as well as the irritable bowel syndrome. The compounds with an affinity for the $5\text{-}HT_6$ receptor are useful for treating anxiety, depression and cognitive memory disorders [M. Yoshioka, et al., *Ann. NY Acad. Sci.*, 1998, 861, 244; A. Bourson, et al., *Br. J. Pharmacol.*, 1998, 125, 1562; D. C. Rogers, et al., *Br. J. Pharmacol. Suppl.*, 1999, 127, 22P; A. Bourson, et al., *J. Pharmacol. Exp. Ther.*, 1995, 274, 173; A. J. Sleight, et al., *Behav. Brain Res.*, 1996, 73, 245; T. A. Branchek, et al., *Annu. Rev. Pharmacol. Toxicol.*, 2000, 40, 319; C. Routledge, et al., *Br. J. Pharmacol.*, 2000, 130, 1606]. It has been shown that the typical and atypical antipsychotics for treating schizophrenia have a high affinity for the $5\text{-}HT_6$ receptors [B. L. Roth, et al., *J. Pharmacol. Exp. Ther.*, 1994, 268, 1403; C. E. Glatt, et al., *Mol. Med.*, 1995, 1, 398; F. J. Mosma, et al., *Mol. Pharmacol.*, 1993, 43, 320; T. Shinkai, et al, *Am. J. Med. Genet.*, 1999, 88, 120]. The compounds with an affinity for the $5\text{-}HT_6$ receptor are useful for treating infantile hyperkinesia (ADHD, attention deficit/hyperactivity disorder) [W. D. Hirst, et al., *Br. J. Pharmacol.*, 2000, 130, 1597; C. Gérard, et al., *Brain Research*, 1997, 746, 207; M. R. Pranzatelli, *Drugs of Today*, 1997, 33, 379].

Patent application WO 01/32646 discloses sulfonamides derived from bicycles, whereby each of the rings is 6-membered, aromatic or heteroaromatic rings with $5\text{-}HT_6$ receptor antagonist activity.

Patent application EP 0 733 628 discloses sulfonamides derived from indole with $5\text{-}HT_{1F}$ receptor antagonist activity, useful for the treatment of migraines.

Furthermore, it has been shown that the $5\text{-}HT_6$ receptor plays a role in the ingestion of food [Neuropharmacology, 41, 2001, 210-219].

Eating disorders, particularly obesity, are a serious and increasingly frequent threat for the health of humans from all ages, since these diseases increase the risk of developing other serious and even mortal diseases, preferably diabetes and coronary artery diseases.

Therefore, an object of the present invention was to provide new compounds, particularly suitable as active substances in medicaments, preferably in medicaments for $5\text{-}HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and multiple sclerosis, schizophrenia, psychosis or infantile hyperkinesia (ADHD, attention deficit/hyperactivity disorder), and other disorders mediated by the $5\text{-}HT_6$ serotonin receptor in humans and/or in animals, preferably in mammals, more preferably in humans.

It has been found that the indol-6-yl sulfonamide compounds of general formulas (Ia, Ib, Ic) described below show an affinity for the $5\text{-}HT_6$ receptor. These compounds are therefore suitable for the manufacture of a medicament for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and multiple sclerosis, schizophrenia, psychosis or infantile hyperkinesia (ADHD, attention deficit/hyperactivity disorder) and other disorders mediated by the $5\text{-}HT_6$ serotonin receptor in humans and/or in animals, preferably in mammals, more preferably in humans.

Thus, one aspect of the present invention are compounds of general formula (Ia),

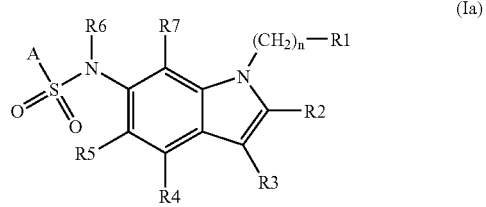

(Ia)

wherein
R$^1$ represents a —NR$^8$R$^9$ radical or a saturated or unsaturated, optionally at least mono-substituted, optionally at least one heteroatom as a ring member containing cycloaliphatic radical, which may be condensed with a saturated or unsaturated, optionally at least mono-substituted, optionally at least one heteroatom as a ring member containing mono- or bicyclic cycloaliphatic ring system, $R^2$, $R^3$, $R^4$, $R^5$ and $R^7$, identical or different, each represent hydrogen, halogen, nitro, alkoxy, cyano, a saturated or unsaturated, linear or branched, optionally at least mono-substituted aliphatic radical, or an optionally at least mono-substituted phenyl or optionally at least mono-substituted heteroaryl radical, $R^6$ represents hydrogen or a saturated or unsaturated, linear or branched, optionally at least mono-substituted aliphatic radical, $R^8$ and $R^9$, identical or different, each represent hydrogen or a saturated or unsaturated, linear or branched, optionally at least mono-substituted aliphatic radical, with the proviso that $R^8$ and $R^9$ are not hydrogen at the same time, and if one of them, $R^8$ or $R^9$, is a saturated or unsaturated, linear or branched, optionally at least mono-substituted $C_1$-$C_4$ aliphatic radical, the other one is a saturated or unsaturated, linear or branched, optionally at least mono-substituted aliphatic radical with at least five carbon atoms, or $R^8$ and $R^9$, together with the bridging nitrogen atom, form a saturated or unsaturated, optionally at least mono-substituted heterocyclic ring, which may contain at least one further heteroatom as a ring member and/or which may be condensed with a saturated or unsaturated, optionally at least mono-substituted, optionally at least one heteroatom as a ring member containing mono- or bicyclic cycloaliphatic ring system, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings, and n is 0, 1, 2, 3 or 4;

optionally in form of one of its stereoisomers, preferably enantiomers or diastereomers, a racemate or in form of a mixture of at least two of its stereoisomers, preferably enantiomers and/or diastereomers, in any mixing ratio, or a salt thereof, preferably a corresponding, physiologically acceptable salt thereof, or a corresponding solvate thereof.

Another aspect of the present invention are compounds of general formula (Ib)

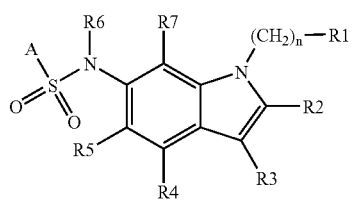

(Ib)

wherein $R^1$ is a —$NR^8R^9$ radical, $R^2$, $R^3$, $R^4$, $R^5$ and $R^7$, identical or different, each represent hydrogen, halogen, nitro, alkoxy, cyano, a saturated or unsaturated, linear or branched, optionally at least mono-substituted aliphatic radical, or an optionally at least mono-substituted phenyl or optionally at least mono-substituted heteroaryl radical, $R^6$ represents hydrogen or a saturated or unsaturated, linear or branched, optionally at least mono-substituted aliphatic radical, $R^8$ and $R^9$, identical or different, each represent hydrogen or a saturated or unsaturated, linear or branched, optionally at least mono-substituted $C_1$-$C_4$ aliphatic radical, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings, n is 0, 1, 2, 3 or 4;

optionally in form of one of its stereoisomers, preferably enantiomers or diastereomers, a racemate or in form of a mixture of at least two of its stereoisomers, preferably enantiomers and/or diastereomers, in any mixing ratio, or a salt thereof, preferably a corresponding, physiologically acceptable salt thereof, or a corresponding solvate thereof.

Yet, another aspect of the present invention are compounds of general formula (Ic),

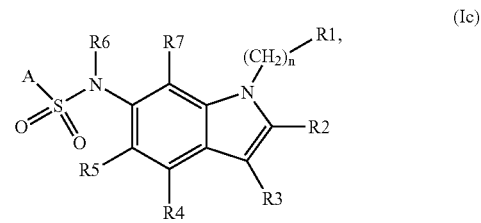

(Ic)

wherein $R^1$ represents a —$NR^8R^9$ radical or a saturated or unsaturated, optionally at least mono-substituted, optionally at least one heteroatom as a ring member containing cycloaliphatic radical, which may be condensed with a saturated or unsaturated, optionally at least mono-substituted, optionally at least one heteroatom as a ring member containing mono- or bicyclic cycloaliphatic ring system, $R^2$, $R^3$, $R^4$, $R^5$ and $R^7$, identical or different, each represent hydrogen, halogen, nitro, alkoxy, cyano, a saturated or unsaturated, linear or branched, optionally at least mono-substituted aliphatic radical, or an optionally at least mono-substituted phenyl or optionally at least mono-substituted heteroaryl radical, $R^6$ represents hydrogen or a saturated or unsaturated, linear or branched, optionally at least mono-substituted aliphatic radical, $R^8$ and $R^9$, identical or different, each represent hydrogen or a saturated or unsaturated, linear or branched, optionally at least mono-substituted aliphatic radical, or $R^8$ and $R^9$, together with the bridging nitrogen atom, form a saturated or unsaturated, optionally at least mono-substituted heterocyclic ring, which may contain at least one further heteroatom as a ring member and/or which may be condensed with a saturated or unsaturated, optionally at least mono-substituted, optionally at least one heteroatom as a ring member containing mono- or bicyclic cycloaliphatic ring system, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings, and n is 0, 1, 2, 3 or 4;

optionally in form of one of its stereoisomers, preferably enantiomers or diastereomers, a racemate or in form of a mixture of at least two of its stereoisomers, preferably enantiomers and/or diastereomers, in any mixing ratio, or a salt thereof, preferably a corresponding, physiologically acceptable salt thereof, or a corresponding solvate thereof.

If one or more of the moieties $R^2$ to $R^9$ represents a saturated or unsaturated aliphatic radical, that is, an alkyl, alkenyl or alkynyl radical, which is substituted by one or more substituents, each one of these substituents may preferably be chosen, unless otherwise defined, from the group consisting of hydroxy, fluorine, chlorine, bromine and trifluoromethyl.

If $R^1$ is a saturated or unsaturated, optionally at least one heteroatom as a ring member containing cycloaliphatic radical, which is substituted by one or more substituents and/or is condensed with a saturated or unsaturated, optionally at least mono-substituted, optionally at least one heteroatom as a ring member containing mono- or bicyclic cycloaliphatic ring system, each of these substituents may, unless otherwise defined, preferably be chosen from the group consisting of hydroxy, fluorine, chlorine, bromine, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl, more preferably chosen from the group consisting of linear or branched $C_1$-$C_6$ alkyl and benzyl.

The heteroatoms of said cycloaliphatic radical and/or of the mono- or bicyclic cycloaliphatic ring may, independently from one another, be chosen preferably from the group consisting of nitrogen, sulphur and oxygen, more preferably nitrogen is chosen as a heteroatom.

Said cycloaliphatic radical may contain 0, 1, 2 or 3 heteroatoms chosen from the above mentioned group, preferably it contains 0, 1 or 2 heteroatoms chosen from the above mentioned group.

If $R^8$ and $R^9$ together with the bridging nitrogen atom form a saturated or unsaturated, optionally at least mono-substituted heterocyclic ring, which may contain at least one further heteroatom as a ring member and/or which may be condensed with a saturated or unsaturated, optionally at least mono-substituted, optionally one heteroatom as a ring member containing mono- or bicyclic ring system, each one of these substituents may, unless otherwise defined, preferably be chosen from the group consisting of hydroxy, fluorine, chlorine, bromine, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy and benzyl, more preferably from the group consisting of linear or branched $C_1$-$C_6$ alkyl and benzyl.

If the heterocyclic ring contains one or more additional heteroatoms, and/or if one or both mono- or bicyclic rings contain one or more additional heteroatoms, these heteroatoms may, independently from one another, preferably be chosen from the group consisting of nitrogen, sulphur and oxygen, more preferably nitrogen is chosen as a heteroatom.

Said heterocyclic ring may contain 0, 1, 2 or 3 additional heteroatoms chosen from the above mentioned group, preferably it contains 0 or 1 heteroatoms chosen from the above mentioned group.

If A is an optionally at least one heteroatom as a ring member containing mono- or polycyclic aromatic ring system, which may be bonded via an optionally at least mono-substituted alkylene, alkenylene or alkynylene group and which may be substituted by one or more substituents, each of these substituents may preferably be chosen, unless otherwise defined, from the group consisting of hydroxy, halogen, linear or branched $C_1$-$C_6$ alkyl, linear or branched $C_1$-$C_6$ alkoxy, —O-phenyl, linear or branched $C_1$-$C_6$ perfluoroalkyl, linear or branched $C_1$-$C_6$ perfluoroalkoxy, an optionally at least mono-substituted phenyl and 5- to 6-membered heteroaryl, more preferably from the group consisting of halogen, linear or branched $C_1$-$C_6$ alkyl, —O-phenyl, optionally at least mono-substituted phenyl and 5- to 6-membered heteroaryl, even more preferably from the group consisting of fluorine, chlorine, —O-phenyl, linear or branched $C_1$-$C_6$ alkyl, optionally at least mono-substituted phenyl and 5- to 6-membered heteroaryl.

If one or more of the rings of a mono- or polycyclic aromatic ring system contain one or more heteroatoms, these heteroatoms—like the heteroatoms of the previously mentioned 5- to 6-membered heteroaryl—may preferably be chosen from the group consisting of nitrogen, sulphur and oxygen.

If the previously mentioned phenyl radical is itself substituted by one or more substituents, each one of these substituents may preferably be chosen from the group consisting of fluorine, chlorine, bromine, linear or branched $C_1$-$C_6$ alkyl, linear or branched $C_1$-$C_6$ alkoxy, linear or branched $C_1$-$C_6$ alkylthio, trifluoromethyl radical, cyano radical and a —$NR^{12}R^{13}$ radical, wherein $R^{12}$ and $R^{13}$, identical or different, each represent hydrogen or linear or branched $C_1$-$C_6$ alkyl.

If the previously mentioned alkylene, alkenylene or alkynylene group is substituted by one or more substituents, each of these substituents may preferably be chosen from the group consisting of hydroxy, halogen, linear or branched $C_1$-$C_6$ alkyl, linear or branched $C_1$-$C_6$ alkoxy, linear or branched $C_1$-$C_6$ perfluoroalkyl, linear or branched $C_1$-$C_6$ perfluoroalkoxy or an optionally at least mono-substituted phenyl radical. If said phenyl radical is itself substituted by one or more substituents, each one of these substituents may preferably be chosen from the group consisting of fluorine, chlorine, bromine, linear or branched $C_1$-$C_6$ alkyl, linear or branched $C_1$-$C_6$ alkoxy, linear or branched $C_1$-$C_6$ alkylthio, trifluoromethyl radical, cyano radical and a —$NR^{12}R^{13}$ radical, wherein $R^{12}$ and $R^{13}$, identical or different, each represent hydrogen or linear or branched $C_1$-$C_6$ alkyl.

If one or more of the substituents $R^2$, $R^3$, $R^4$, $R^5$ and $R^7$ represents an alcoxy radical, said radical may have 1 to 6, preferably 1 to 3 carbon atoms.

Those skilled in the art understand that the term "condensed" indicates that the condensed rings share more than one atom. The terms "annulated" or "fused" may also be used for this type of bonding.

Sulfonamide derivatives of general formula (Ia) are preferred, wherein $R^1$ represents a —$NR^8R^9$ radical or a saturated or unsaturated, optionally at least mono-substituted, optionally at least one heteroatom as a ring member containing 5- or 6-membered cycloaliphatic radical, which may be condensed with a saturated or unsaturated, optionally at least mono-substituted, optionally at least one heteroatom as a ring member containing mono- or bicyclic cycloaliphatic ring system, whereby the rings of the ring system are 5- or 6-membered, more preferably $R^1$ represents an —$NR^8R^9$ radical or a radical chosen from the group consisting of

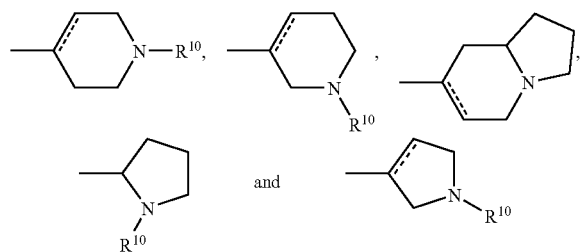

wherein, if present, the dotted line represents an optional chemical bond, and $R^{10}$ represents hydrogen, a linear or branched $C_1$-$C_6$ alkyl radical or a benzyl radical, preferably hydrogen or a $C_1$-$C_2$ alkyl radical and $R^2$ to $R^9$, A and n are defined as above.

Also preferred are sulfonamide derivatives of general formula (Ia), wherein $R^2$, $R^3$, $R^4$, $R^5$ and $R^7$, identical or different, each represent hydrogen, a linear or branched $C_1$-$C_6$ alkoxy radical, a linear or branched, optionally at least mono-substituted $C_1$-$C_6$ alkyl radical, a linear or branched, optionally at least mono-substituted $C_2$-$C_6$ alkenyl radical, or a linear or branched, optionally at least mono-substituted $C_2$-$C_6$ alkynyl radical, more preferably $R^2$, $R^3$, $R^4$, $R^5$ and $R^7$, identical or different, each represent hydrogen or a linear or branched, optionally at least mono-substituted $C_1$-$C_6$ alkyl radical, even more preferably $R^2$, $R^3$, $R^4$, $R^5$ and $R^7$, identical or different, each represent hydrogen, and $R^1$, $R^6$, $R^8$, $R^9$, A and n are defined as above.

Sulfonamide derivatives of general formula (Ia) are also preferred, wherein $R^6$, represents hydrogen, a linear or branched, optionally at least mono-substituted $C_1$-$C_6$ alkyl radical, a linear or branched, optionally at least mono-substituted $C_2$-$C_6$ alkenyl radical, a linear or branched, optionally at least mono-substituted $C_2$-$C_6$ alkynyl radical, more preferably $R^6$ represents hydrogen or a linear or branched, optionally at least mono-substituted $C_1$-$C_6$ alkyl radical, even more preferably $R^6$ represents hydrogen or a $C_1$-$C_2$ alkyl radical, and $R^1$-$R^5$, $R^7$-$R^9$, A and n are defined as above.

Furthermore, sulfonamide derivatives of general formula (Ia) are also preferred, wherein $R^8$ and $R^9$, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical, a linear or branched, optionally at least mono-substituted $C_2$-$C_{10}$ alkynyl radical, with the proviso that $R^8$ and $R^9$ do not represent hydrogen at the same time, and if one of them, $R^8$ and $R^9$, represents a saturated or unsaturated, linear or branched, optionally at least mono-substituted $C_1$-$C_4$ aliphatic radical, the other one represents a saturated or unsaturated, linear or branched, optionally at least mono-substituted aliphatic radical with at least five carbon atoms, or $R^8$ and $R^9$, together with the bridging nitrogen form a saturated or unsaturated, optionally at least mono-substituted, optionally at least one further heteroatom as a ring member containing 5- or 6-membered heterocyclic ring, which may be condensed with a saturated or unsaturated, optionally at least mono-substituted, optionally at least one heteroatom as a ring member containing mono- or bicyclic cycloaliphatic ring system, whereby the rings of the ring system are 5-6- or 7-membered, and $R^1$-$R^7$, A and n are defined as above.

Particularly preferred are sulfonamide derivatives of general formula (Ia), wherein $R^8$ and $R^9$, identical or different, each represent hydrogen or a linear or branched $C_1$-$C_{10}$ alkyl radical, with the proviso that $R^8$ and $R^9$ are not hydrogen at the same time, and if one of them, $R^8$ or $R^9$, is a saturated or unsaturated, linear or branched, optionally at least mono-substituted $C_1$-$C_4$ aliphatic radical, the other one of them is a saturated or unsaturated, linear or branched, optionally at least mono-substituted aliphatic radical with at least five carbon atoms, or $R^8$ and $R^9$ together with the bridging nitrogen atom form a radical chosen from the group consisting of

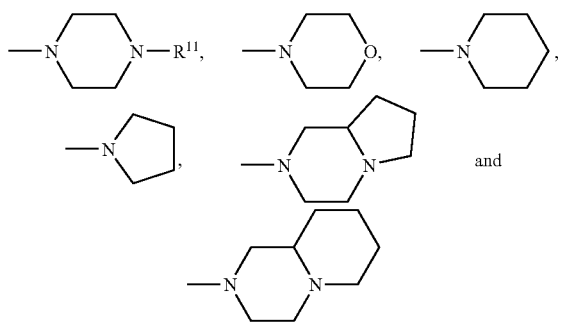

wherein $R^{11}$ represents hydrogen, a linear or branched $C_1$-$C_6$ alkyl radical or a benzyl radical, preferably hydrogen or a $C_1$-$C_2$ alkyl radical, and $R^1$-$R^7$, A and n are defined as above.

Furthermore, sulfonamide derivatives of general formula (Ia) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member, preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

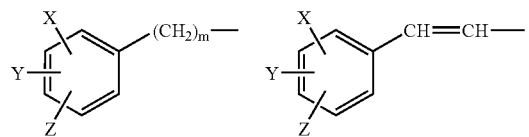

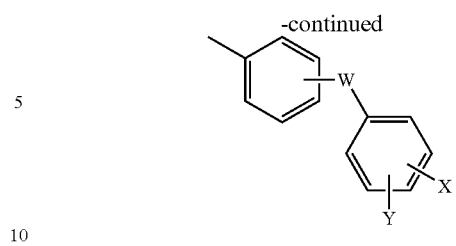

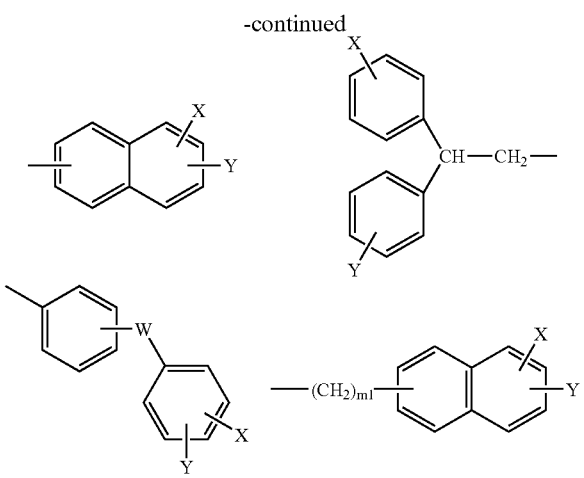

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2, and $R^1$-$R^9$ and n are defined as above.

Furthermore, sulfonamide derivatives of general formula (Ia) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group, and/or wherein the ring(s) may contain at least one heteroatom as a ring member, more preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

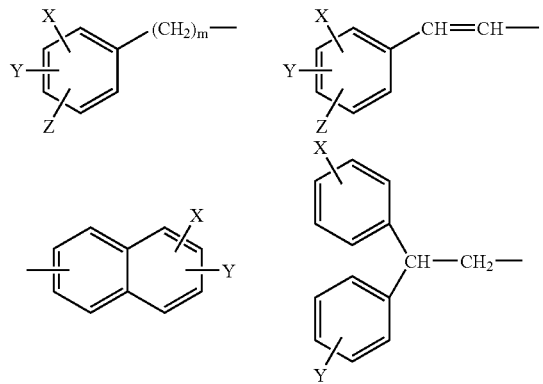

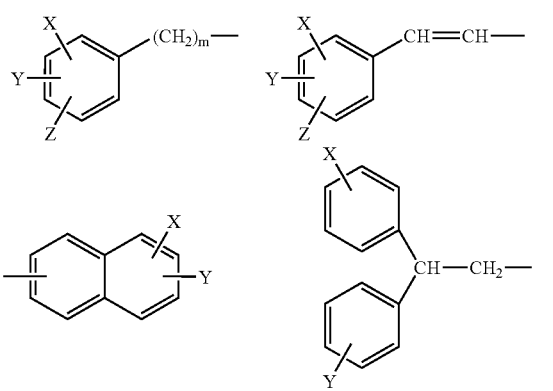

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, and m is 0, 1, 2, 3 or 4.

and $R^1$-$R^9$ and n are defined as above.

Furthermore, sulfonamide derivatives of general formula (Ia) are preferred, wherein A represents an heteroaryl radical selected from the group consisting of benzo[b]thiophenyl and imidazo[2,1-b]thiazolyl which may be substituted by 1, 2 or 3 substituents selected from the group consisting of chlorine, methyl, phenyl and —O-phenyl and/or which may be bonded via a $C_{1-2}$ alkylene group, or a radical chosen from the group consisting of wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2, and $R^1$-$R^9$ and n are defined as above.

Furthermore sulfonamide derivatives of general formula (Ia) are preferred, wherein n is 0, 1, 2, 3 or 4; preferably n is 1 or 2; more preferably n is 2 and $R^1$ to $R^9$ and A are defined as above.

Those most preferred compounds of general formula (Ia) are selected from the group consisting of

[9] 5-Chloro-3-methyl-N-[1-[2-(pyrrolidin-1-yl)ethyl-1H-indol-6-yl]-benzo[b]thiophene-2-sulfonamide,

[10] N-(1-[2-(Pyrrolidin-1-yl)ethyl]-1H-indol-6-yl]-napthalalene-2-sulfonamide,

[11] N-[1-[2-Pyrrolidin-1-yl]ethyl]-1H-indol-6-yl]-naphthalene-1-sulfonamide,

[12] 6-Chloro-N-[1-[2-(pyrrolidin-1-yl)ethyl]-1H-indol-6-yl]-imidazo[2,1-b]thiazole-5-sulfonamide,

[13] 4-Phenyl-N-(1-(2-(pyrrolidin-1-yl)ethyl)-1H-indol-6-yl)-benzenesulfonamide

[14] 2-(Naphth-1-yl)-N-(1-(2-(pyrrolidin-1-yl)-ethyl)-1H-indol-6-yl)-ethansulfonamide,

[15] 4-Phenoxy-N-(1-(2-(pyrrolidin-1-yl)ethyl)-1H-indol-6-yl)-benzenesulfonamide and

[16] 3,5-Dichloro-N-(1-(2-(pyrrolidin-1-yl)-1H-indol-6-yl)-benzenesulfonamide, and their corresponding salts and solvates.

Furthermore, sulfonamide derivatives of general formula (Ib) are also preferred, wherein $R^2$, $R^3$, $R^4$, $R^5$ and $R^7$, identical or different, each represent hydrogen, $C_1$-$C_6$ alkoxy radical, a linear or branched, optionally at least mono-substituted $C_2$-$C_6$ alkyl radical, a linear or branched, optionally at least mono-substituted $C_2$-$C_6$ alkenyl radical, or a linear or branched, optionally at least mono-substituted $C_2$-$C_6$ alkynyl radical, more preferably $R^2$, $R^3$, $R^4$, $R^5$ and $R^7$, identical or different, each represent hydrogen or a linear or branched, optionally at least mono-substituted $C_1$-$C_6$ alkyl radical, even more preferably $R^2$, $R^3$, $R^4$, $R^5$ and $R^7$, identical or different, each represent hydrogen, and $R^1$, $R^6$, $R^8$, $R^9$, A and n are defined as above.

Sulfonamide derivatives of general formula (Ib) are also preferred, wherein $R^6$ represents hydrogen, a linear or branched, optionally at least mono-substituted $C_1$-$C_6$ alkyl radical, a linear or branched, optionally at least mono-substituted $C_2$-$C_6$ alkenyl radical, a linear or branched, optionally at least mono-substituted $C_2$-$C_6$ alkynyl radical, more preferably $R^6$ represents hydrogen or a linear or branched, optionally at least mono-substituted $C_1$-$C_6$ alkyl radical, more preferably $R^6$ represents hydrogen or a $C_1$-$C_2$ alkyl radical, and $R^1$-$R^5$, $R^7$-$R^9$, A and n are defined as above.

Furthermore, sulfonamide derivatives of general formula (Ib) are also preferred, wherein $R^8$ and $R^9$, identical or different, each represent hydrogen or a linear or branched, optionally at least mono-substituted $C_1$-$C_4$ alkyl radical, and $R^1$-$R^7$, A and n are defined as above.

Particularly preferred are sulfonamide derivatives of general formula (Ib) wherein $R^8$ and $R^9$, identical or different, each represent hydrogen or a $C_1$-$C_2$ alkyl radical, with the proviso that $R^8$ and $R^9$ are not hydrogen at the same time, and $R^1$-$R^7$, A and n are defined as above.

Furthermore, sulfonamide derivatives of general formula (Ib) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member, preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

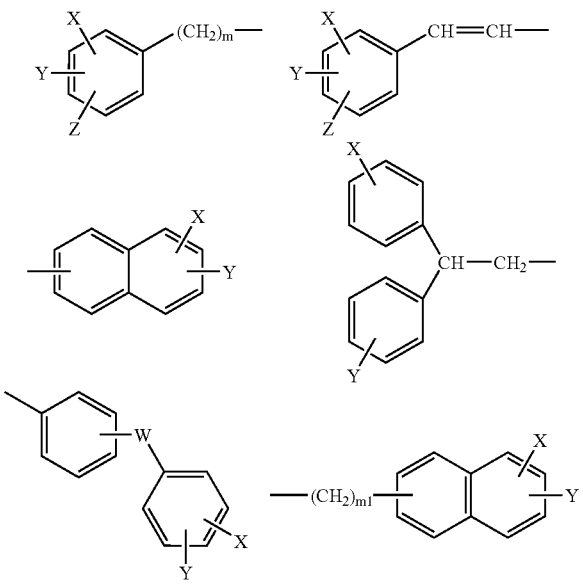

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2 and $R^1$-$R^9$ and n are defined as above.

Furthermore, sulfonamide derivatives of general formula (Ib) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group, and/or wherein the ring(s) may contain at least one heteroatom as a ring member, more preferably A represents an optionally at least monosubstituted mono- or polycyclic aromatic ring system, wherein the ring(s) is/are 5- or 6-membered and wherein one or more of the rings contain at least one heteroatom, or a radical chosen from the group consisting of

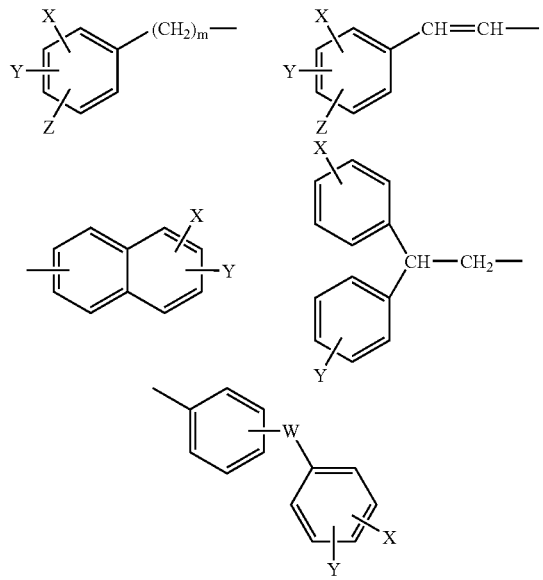

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, and m is 0, 1, 2, 3 or 4.

and $R^1$-$R^9$ and n are defined as above.

Furthermore, sulfonamide derivatives of general formula (Ib) are preferred, wherein A represents an heteroaryl radical selected from the group consisting of benzo[b]thiophenyl and imidazo[2,1-b]thiazolyl which may be substituted by 1, 2 or 3 substituents selected from the group consisting of chlorine, methyl, phenyl and —O-phenyl and/or which may be bonded via a $C_{1-2}$ alkylene group, or a radical chosen from the group consisting of

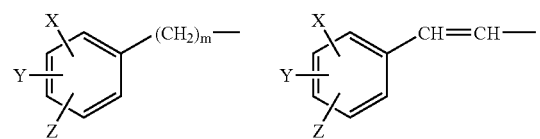

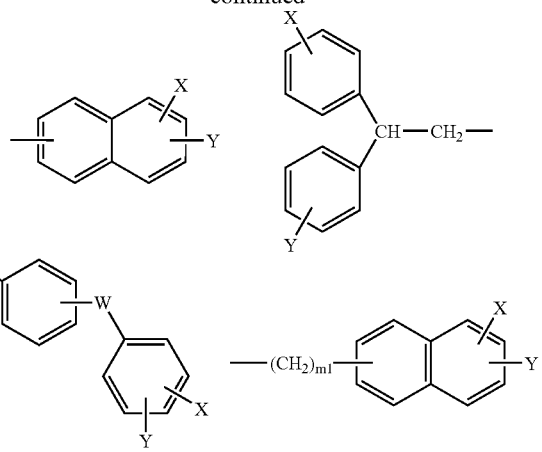

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2, preferably 2 and $R^1$-$R^9$ and n are defined as above Furthermore sulfonamide derivatives of general formula (Ib) are preferred, wherein n is 0, 1, 2, 3 or 4; preferably n is 1 or 2; more preferably n is 2 and $R^1$ to $R^9$ and A are defined as above.

Those most preferred compounds are sulfonamide derivatives of general formula (Ib), selected from the group consisting of

[1] N-[1-(2-Dimethylaminoethyl)-1H-indol-6-yl]-5-chloro-3-methylbenzo[b]thiophene-2-sulfonamide,

[2] N-[1-(2-Dimethylaminoethyl)-1H-indol-6-yl]-naphthalene-2-sulfonamide,

[3] N-[1-(2-Dimethylaminoethyl)-1H-indol-6-yl]-naphthalene-1-sulfonamide,

[4] N-[1-(2-Dimethylaminoethyl)-1H-indol-6-yl]-6-chloroimidazo[2,1-b]thiazole-5-sulfonamide,

[5] N-[1-(2-Dimethylaminoethyl)-1H-indol-6-yl]-4-phenylbenzenesulfonamide,

[6] N-[1-(2-Dimethylaminoethyl)-1H-indol-6-yl]-2-(naphthalene-1-yl)-ethanesulfonamide,

[7] N-[1-(2-Dimethylaminoethyl)-1H-indol-6-yl]-4-phenoxybenzenesulfonamide,

[8] N-[1-(2-Dimethylaminoethyl)-1H-indol-6-yl]-3,5-dichlorobenzenesulfonamide, and their corresponding salts and solvates.

Furthermore, sulfonamide derivatives of general formula (Ic) are preferred, wherein $R^1$ represents a —$NR^8R^9$ radical or a saturated or unsaturated, optionally at least mono-substituted, optionally at least one heteroatom as a ring member containing 5- or 6-membered cycloaliphatic radical, which may be condensed with a saturated or unsaturated, optionally at least mono-substituted, optionally at least one heteroatom as a ring member containing mono- or bicyclic cycloaliphatic ring system, whereby the rings of the ring system are 5- or 6-membered, more preferably $R^1$ represents an —$NR^8R^9$ radical or a radical chosen from the group consisting of

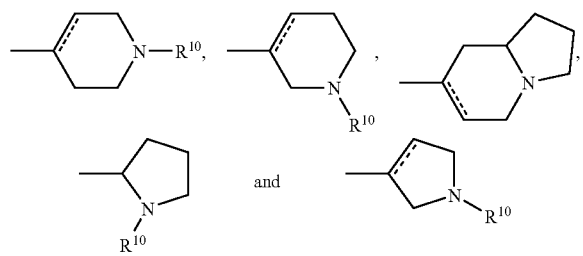

wherein, if present, the dotted line represents an optional chemical bond, and $R^{10}$ represents hydrogen, a linear or branched $C_1$-$C_6$ alkyl radical or a benzyl radical, preferably hydrogen or a $C_1$-$C_2$ alkyl radical and $R^2$ to $R^9$, A and n are defined as above.

Also preferred are sulfonamide derivatives of general formula (Ic), wherein $R^2$, $R^3$, $R^4$, $R^5$ and $R^7$, identical or different, each represent hydrogen, a linear or branched $C_1$-$C_6$ alkoxy radical, a linear or branched, optionally at least mono-substituted $C_1$-$C_6$ alkyl radical, a linear or branched, optionally at least mono-substituted $C_2$-$C_6$ alkenyl radical, or a linear or branched, optionally at least mono-substituted $C_2$-$C_6$ alkynyl radical, more preferably $R^2$, $R^3$, $R^4$, $R^5$ and $R^7$, identical or different, each represent hydrogen or a linear or branched, optionally at least mono-substituted $C_1$-$C_6$ alkyl radical, even more preferably $R^2$, $R^3$, $R^4$, $R^5$ and $R^7$, identical or different, each represent hydrogen, and $R^1$, $R^6$, $R^8$, $R^9$, A and n are defined as above.

Sulfonamide derivatives of general formula (Ic) are also preferred, wherein $R^6$, represents hydrogen, a linear or branched, optionally at least mono-substituted $C_1$-$C_6$ alkyl radical, a linear or branched, optionally at least mono-substituted $C_2$-$C_6$ alkenyl radical, a linear or branched, optionally at least mono-substituted $C_2$-$C_6$ alkynyl radical, more preferably $R^6$ represents hydrogen or a linear or branched, optionally at least mono-substituted $C_1$-$C_6$ alkyl radical, even more preferably $R^6$ represents hydrogen or a $C_1$-$C_2$ alkyl radical, and $R^1$-$R^5$, $R^7$-$R^9$, A and n are defined as above.

Furthermore, sulfonamide derivatives of general formula (Ic) are also preferred, wherein $R^8$ and $R^9$, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical, a linear or branched, optionally at least mono-substituted $C_2$-$C_{10}$ alkynyl radical, or $R^8$ and $R^9$, together with the bridging nitrogen form a saturated or unsaturated, optionally at least mono-substituted, optionally at least one further heteroatom as a ring member containing 5- or 6-membered heterocyclic ring, which may be condensed with a saturated or unsaturated, optionally at least mono-substituted, optionally at least one heteroatom as a ring member containing mono- or bicyclic cycloaliphatic ring system, whereby the rings of the ring system are 5-6- or 7-membered, and $R^1$-$R^7$, A and n are defined as above.

Particularly preferred are sulfonamide derivatives of general formula (Ic), wherein $R^8$ and $R^9$, identical or different, each represent hydrogen or a linear or branched $C_1$-$C_{10}$ alkyl radical, or $R^8$ and $R^9$ together with the bridging nitrogen atom form a radical chosen from the group consisting of

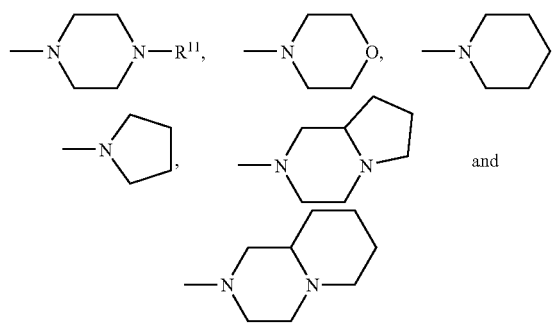

wherein $R^{11}$ represents hydrogen, a linear or branched $C_1$-$C_6$ alkyl radical or a benzyl radical, preferably hydrogen or a $C_1$-$C_2$ alkyl radical, and $R^1$-$R^7$, A and n are defined as above.

Furthermore, sulfonamide derivatives of general formula (Ic) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member, preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

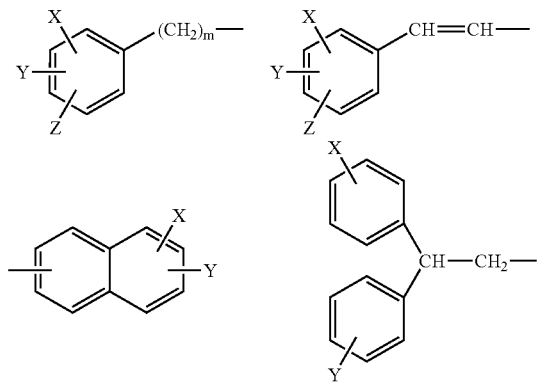

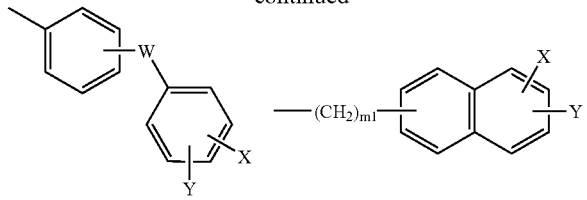

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl,
W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and
m1 is 1 or 2, preferably 2 and $R^1$-$R^9$ and n are defined as above.

Furthermore, sulfonamide derivatives of general formula (Ic) are preferred, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group, and/or wherein the ring(s) may contain at least one heteroatom as a ring member, more preferably A represents an optionally at least mono-substituted mono- or polycyclic aromatic ring system, wherein the ring(s) is/are 5- or 6-membered and wherein one or more of the rings contain at least one heteroatom, or a radical chosen from the group consisting of

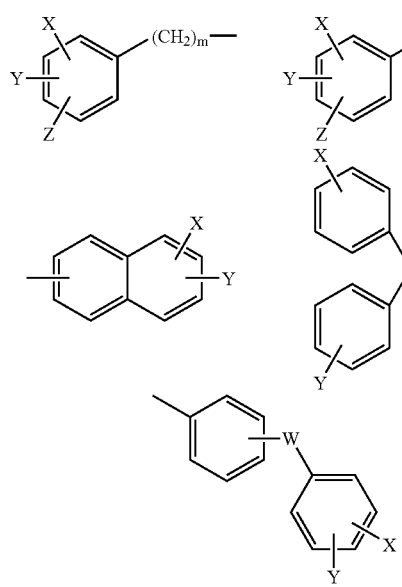

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl,
W represents a single chemical bond between the two rings, a $CH_2$, O, S group or a $NR^{14}$ radical, wherein $R^{14}$ is hydrogen or a linear or branched $C_1$-$C_6$ alkyl, and
m is 0, 1, 2, 3 or 4.
and $R^1$-$R^9$ and n are defined as above.

Furthermore, sulfonamide derivatives of general formula (Ic) are preferred, wherein A represents an heteroaryl radical selected from the group consisting of benzo[b]thiophenyl and imidazo[2,1-b]thiazolyl which may be substituted by 1, 2 or 3 substituents selected from the group consisting of chlorine, methyl, phenyl and —O-phenyl and/or which may be bonded via a $C_{1-2}$ alkylene group, or a radical chosen from the group consisting of

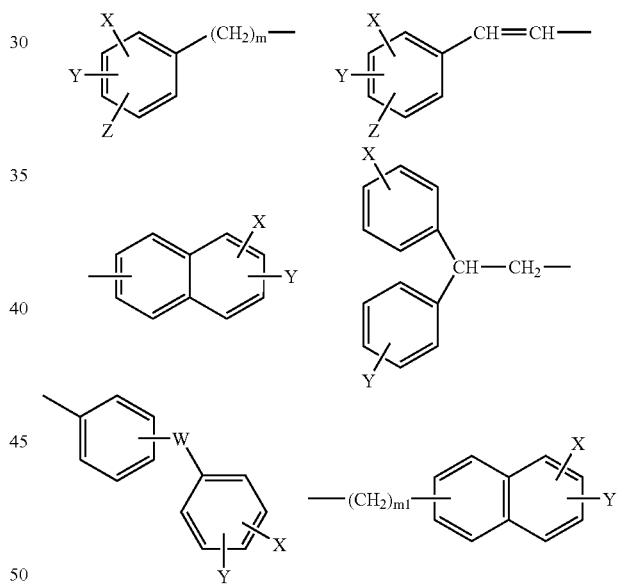

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$alkyl,
W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and
m1 is 1 or 2, preferably 2 and $R^1$-$R^9$ and n are defined as above Furthermore sulfonamide derivatives of general formula (Ic) are preferred, wherein n is 0, 1, 2, 3 or 4; preferably n is 1 or 2; more preferably n is 2 and $R^1$ to $R^9$ and A are defined as above.

Another aspect of the present invention are compounds of general formula (Ic),

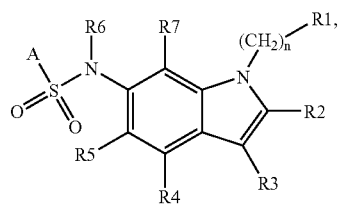

wherein
$R^1$ represents a —$NR^8R^9$ radical,
$R^2$, $R^3$, $R^4$, $R^5$ and $R^7$ each represent hydrogen,
$R^6$ represents hydrogen,
$R^8$ and $R^9$, identical or different, each represent methyl, ethyl, n-propyl or n-propyl, more preferably methyl, or $R^8$ and $R^9$, together with the bridging nitrogen atom form a 5- or 6-membered heterocyclic ring, more preferably form a pyrrolidine ring or a piperidine ring and A represents an aryl or heteroaryl radical selected from the group consisting of phenyl, naphthyl, benzo[b]thiophenyl and imidazo[2,1-b]thiazolyl which may be substituted by 1, 2 or 3 substituents selected from the group consisting of chlorine, methyl, phenyl and —O-phenyl and/or which may be bonded via a $C_{1-2}$ alkylene group, and n is 2, optionally in form of one of its stereoisomers, preferably enantiomers or diastereomers, a racemate or in form of a mixture of at least two of its stereoisomers, preferably enantiomers and/or diastereomers, in any mixing ratio, or a salt thereof, preferably a corresponding, physiologically acceptable salt thereof, or a corresponding solvate thereof.

Those most preferred compounds are sulfonamide derivatives of general formula (Ic), selected from the group consisting of

[1] N-[1-(2-Dimethylaminoethyl)-1H-indol-6-yl]-5-chloro-3-methylbenzo[b]thiophene-2-sulfonamide,
[2] N-[1-(2-Dimethylaminoethyl)-1H-indol-6-yl]-naphthalene-2-sulfonamide,
[3] N-[1-(2-Dimethylaminoethyl)-1H-indol-6-yl]-naphthalene-1-sulfonamide,
[4] N-[1-(2-Dimethylaminoethyl)-1H-indol-6-yl]-6-chloroimidazo[2,1-b]thiazole-5-sulfonamide,
[5] N-[1-(2-Dimethylaminoethyl)-1H-indol-6-yl]-4-phenylbenzenesulfonamide,
[6] N-[1-(2-Dimethylaminoethyl)-1H-indol-6-yl]-2-(naphthalene-1-yl)-ethanesulfonamide,
[7] N-[1-(2-Dimethylaminoethyl)-1H-indol-6-yl]-4-phenoxybenzenesulfonamide,
[8] N-[1-(2-Dimethylaminoethyl)-1H-indol-6-yl]-3,5-dichlorobenzenesulfonamide,
[9] 5-Chloro-3-methyl-N-[1-[2-(pyrrolidin-1-yl)ethyl-1H-indol-6-yl]-benzo[b]thiophene-2-sulfonamide,
[10] N-(1-[2-(Pyrrolidin-1-yl)ethyl]-1H-indol-6-yl]-napthyl-2-sulfonamide,
[11] N-[1-[2-Pyrrolidin-1-yl]ethyl]-1H-indol-6-yl]-naphthalene-1-sulfonamide,
[12] 6-Chloro-N-[1-[2-(pyrrolidin-1-yl)ethyl]-1H-indol-6-yl]-imidazo[2,1-b]thiazole-5-sulfonamide,
[13] 4-Phenyl-N-(1-(2-(pyrrolidin-1-yl)ethyl)-1H-indol-6-yl)-benzenesulfonamide
[14] 2-(Naphth-1-yl)-N-(1-(2-(pyrrolidin-1-yl)ethyl)-1H-indol-6-yl)-ethansulfonamide,
[15] 4-Phenoxy-N-(1-(2-(pyrrolidin-1-yl)ethyl)-1H-indol-6-yl)-benzenesulfonamide and
[16] 3,5-Dichloro-N-(1-(2-(pyrrolidin-1-yl)-1H-indol-6-yl)-benzenesulfonamide, and their corresponding salts and solvates.

The present invention likewise refers to the salts, preferably the physiologically acceptable salts of the compounds of general formula (Ia) and/or (Ib) and/or of general formula (Ic), preferably the addition salts of mineral acids, more preferably of hydrochloric acid, hydrobromic acid acid, phosphoric acid, sulphuric acid, nitric acid, and the salts of organic acids, more preferably of citric acid, maleic acid acid, fumaric acid, tartaric acid or their derivatives, p-toluenesulphonic acid, methanesulphonic acid, camphorsulphonic acid, etc.

Below, the expression sulfonamide derivatives of general formula (I) refers to one or more compounds of general formula (Ia) and/or to one or more compounds of general formula (Ib) and/or to one or more compounds of general formula (Ic), respectively, and optionally in form of one of their stereoisomers, preferably enantiomers or diastereomers, their racemate, or in form of a mixture of at least two of their stereoisomers, preferably enantiomers or diastereomers, in any mixing ratio, or a salt thereof, preferably a corresponding physiologically acceptable salt thereof, or a corresponding solvate thereof.

Another aspect of the present invention consists of a process for preparing the new derivatives of general formula (I), wherein $R^1$-$R^9$, n and A have the previously indicated meaning, according to which at least one compound of general formula (II),

wherein A has the previously mentioned meaning, and X is an acceptable leaving group, preferably an halogen atom, more preferably chlorine; is reacted with at least one substituted 6-aminoindole of general formula (III), or one of its suitably protected derivatives;

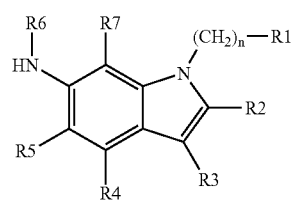

wherein $R^1$-$R^7$ and n have the previously indicated meaning, and, if necessary, the protective groups are removed in order to obtain the corresponding sulfonamide derivative of formula (I), which can be purified and/or isolated by means of conventional methods known in the prior art.

The reaction between the compounds of general formula (II) and (III) is usually carried out in the presence of an organic reaction medium, preferably in the presence of dialkyl ether, more preferably diethyl ether or a cyclic ether, more preferably tetrahydrofuran or dioxane, an halogenated organic hydrocarbon, more preferably methylene chloride or chloroform, an alcohol, more preferably methanol or ethanol, a dipolar aprotic solvent, more preferably acetonitrile, pyridine or dimethylformamide, or any other suitable reaction medium. Naturally, mixtures of at least two of the classes of the mentioned compounds or at least two compounds of one class may also be used.

The reaction is preferably carried out in the presence of a suitable base, for example, an inorganic base, more preferably alkaline metal hydroxides and alkaline metal carbonates, or in the presence of an organic base, more preferably triethylamine, N-ethyldiisopropylamine or pyridine.

The most suitable reaction temperatures range from 0° C. to room temperature, that is, approximately 25° C., and the reaction time preferably comprises from 5 minutes to 24 hours.

The resulting sulfonamide derivative of general formula (I) can be purified and/or isolated according to conventional methods known in the prior art.

Preferably, the sulfonamide derivatives of general formula (I) can be isolated by evaporating the reaction medium, adding water and, if necessary, adjusting the pH so that a solid which can be isolated by filtration is obtained; or it can be extracted with a water immiscible solvent, preferably chloroform, and be purified by chromatography or recrystallization of a suitable solvent.

The compounds of general formula (II) are commercially available, or they can be prepared according to standard methods known in the prior art, for example by methods similar to those described in the literature [E. E. Gilbert, Synthesis, 1969, 1, 3]. The compounds of general formula (III) can also be prepared according to standard methods known in the prior art, for example by methods similar to those described in the literature [Ham, Peter; Gaster, Laramie Mary; King, Francis David; Duckworth, David Malcolm. Preparation of N-heteroaryl-4'-oxadiazolylbiphenylcarboxamides as 5HT1 D antagonists. WO 9532967 A1 19951207; Basanagoudar, L. D.; Siddappa, S. Cyanoethylation of nitroindoles. Journal of the Indian Chemical Society (1972), 49 (8), 811-13.; Chen, Guoqing; Adams, Jeffrey; Bemis, Jean; Booker, Shon; Cai, Guolin; Croghan, Michael; Dipietro, Lucian; Dominguez, Celia; Elbaum, Daniel; Germain, Julie; Geuns-Meyer, Stephanie; Handley, Michael; Huang, Qi; Kim, Joseph L.; Kim, Tae-seong; Kiselyov, Alexander; Ouyang, Xiaohu; Patel, Vinod F.; Smith, Leon M.; Stec, Markian; Tasker, Andrew; Xi, Ning; Xu, Shimin; Yuan, Chester Chenguang. Preparation of heterocyclylalkylamine derivatives as remedies for angiogenesis mediated diseases. WO 0266470 A1 20020829. European Journal of Medicinal Chemistry, 23 (4), 373-7; 1988]. One of them consists of nitro group reduction of derivatives of general formula (IV) by methods known in the art, as for example YAMASHKIN, S. A.; YUROVSKAYA, M. A.; Chem Heterocycl Compd (N.Y.), 1999, 35 (12), 1426-1432. BOOTHROYD, S. R.; KERR, M. A.; Tetrahedron Lett, 1995, 36 (14), 2411-2414. MACOR, J. E.; POST, R.; RYAN, K.; Synth Common, 1993, 23 (1), 65-72,

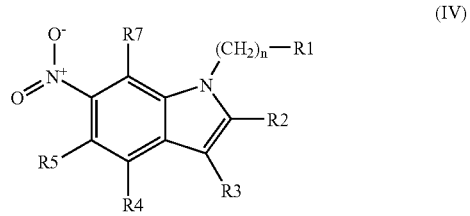

wherein $R^1$-$R^7$ and n have the previously indicated meaning, or one of their suitably protected derivatives, and, if necessary, the protective groups are removed in order to obtain the corresponding amine of general formula (III), which can be purified and/or isolated by means of conventional methods known in the prior art.

The compounds of general formula (IV) can also be prepared according to standard methods known in the prior art, for example by methods similar to those described in the European Journal of Medicinal Chemistry, 23 (4), 373-7; 1988; Farmaco, 51 (1), 75-8; 1996; Heterocycles, 55 (6), 1151-1159; 2001; Ham, Peter; Gaster, Laramie Mary; King, Francis David; Duckworth, David Malcolm. Preparation of N-heteroaryl-4'-oxadiazolylbiphenylcarboxamides as 5HT1D antagonists, WO 9532967 A1 19951207.

One of them consists in the alkylation of nitro derivatives of general formula (IV) by methods known in the art: MACCHIA, M.; MANERA, C.; NENCETTI, S.; ROSSELLO, A.; BROCCALI, G.; LIMONTA, D.; Farmaco, Ed Sci [FRPSAX] 1996, 51 (1), 75-78. BHAGWAT, S. S.; GUDE, C.; Tetrahedron Lett, 1994, 35 (12), 1847-1850. BRATTON, L. D.; ROTH, B. D.; TRIVEDI, B. K.; UNANGST, P. C.; J Heterocycl Chem, 2000, 37 (5), 1103-1108,

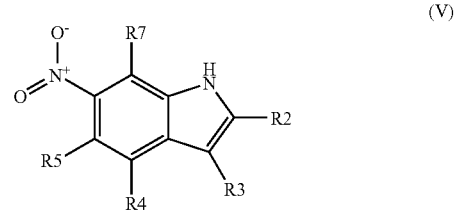

wherein $R^2$-$R^7$ and n have the previously mentioned meaning, or one of their suitably protected derivatives, and, if necessary, the protective groups are removed in order to obtain the corresponding amine of general formula (III), which can be purified and/or isolated by means of conventional methods known in the prior art.

The compounds of general formula (V) are commercially available or can also be prepared according to standard methods known in the prior art, as for example OTTONI, O.; CRUZ, R.; KRAMMER, N. H.; Tetrahedron Lett [TELEAY] 1999, 40 (6), 1117-1120. VOROB'EVA, S. L.; BUYANOV, V. N.; SUVOROV, N. N.; Khim Geterosikl Soedin [KGSSAQ] 1991, (5), 636-637. KATRITZKY, A. R.; RACHWAL, S.; BAYYUK, S.; Org Prep Proceed Int [OPPIAK] 1991, 23 (3), 357-363. MOSKALEV, N.; MAKOSZA, M.; Heterocycles [HTCYAM] 2000, 52 (2), 533-536.

The respective literature descriptions are incorporated by reference and form part of the disclosure.

Another aspect of the present invention consists in a process for preparing the new sulfonamide derivatives of general formula (I), wherein $R^1$-$R^5$, $R^7$-$R^9$, A and n have the previously indicated meaning and $R^6$ is an alkyl radical, preferably a linear or branched, optionally at least mono-substituted $C_1$-$C_6$ alkyl radical, by alkylation of a sulfonamide derivative of general formula (I), wherein $R^1$-$R^5$, $R^7$-$R^9$, n and A have the previously indicated meaning, and $R^6$ is an hydrogen atom, with an alkyl halogenide or dialkyl sulfate.

The alkylation reaction is carried out preferably in the presence of a suitable base, more preferably in the presence of alkaline metal hydroxides and alkaline metal carbonates, metal hydrides, metal alkoxides, even more preferably sodium methoxide or potassium tert-butoxide, organometallic compounds, even more preferably butyllithium or tert-butyllithium, in the presence of an organic reaction medium, more preferably dialkyl ether, even more preferably diethyl ether, or a cyclic ether, even more preferably tetrahydrofuran or dioxane, an hydrocarbon, even more preferably toluene, an alcohol, even more preferably methanol or ethanol, a dipolar aprotic solvent, even more preferably acetonitrile, pyridine or dimethylformamide, or any other suitable reaction medium. Naturally, mixtures of at least two of the classes of the mentioned compounds or at least two compounds of one class may also be used.

The most suitable reaction temperatures range from 0° C. to the boiling temperature of the reaction medium, and the reaction times are preferably comprised from 1 to 24 hours.

Preferably, the resulting sulfonamide derivative of general formula (I) can be isolated by filtration, concentrating the filtrate under reduced pressure, adding water and, if necessary, adjusting the pH so that a solid which can be isolated by filtration is obtained; or it can be extracted with a water immiscible solvent, preferably chloroform, and be purified by chromatography or recrystallization of a suitable solvent.

The salts, preferably pharmaceutically acceptable salts of the compounds of general formula (I), may be prepared by means of conventional methods known in the prior art, preferably by reaction with a mineral acid, more preferably by reaction with hydrochloric acid, hydrobromic acid, phosphoric acid acid, sulphuric acid or nitric acid, or by reaction with organic acids, more preferably by reaction with citric acid, maleic acid, fumaric acid, tartaric acid, or their derivatives, p-toluenesulphonic acid, methanesulphonic acid, camphorsulphonic acid, etc., in a suitable solvent, preferably methanol, ethanol, diethyl ether, ethyl acetate, acetonitrile or acetone, and obtaining the resulting salts by using the usual techniques for the precipitation or crystallization of the corresponding salts.

The preferred physiologically acceptable salts of the sulfonamide derivatives of general formula (I) are the addition salts of mineral acids, more preferably of hydrochloric acid, hydrobromic acid, phosphoric acid, sulphuric acid or nitric acid, and the addition salts of organic acids, more preferably citric acid, maleic acid, fumaric acid, tartaric acid, or their derivatives, p-toluenesulphonic acid, methanesulphonic acid, camphorsulphonic acid, etc.

The solvates, preferably the physiologically acceptable solvates, more preferably hydrates, of the sulfonamide derivatives of general formula (I) or of the corresponding physiologically acceptable salts, may be prepared by methods known in the prior art.

During some of the synthetic sequences described or in the preparation of the suitable reagents used, it may be necessary and/or desirable to protect sensitive or reactive groups in some of the molecules used. This can be done by means of using conventional protective groups preferably those described in the literature [Protective groups in Organic Chemistry, ed. J. F. W. McOmie, Plenum Press, 1973; T. W. Greene & P. G. M. Wuts, Protective Groups in Organic Chemistry, John Wiley & Sons, 1991]. The protective groups can be removed in a suitable subsequent stage by methods known in the prior art. The respective literature descriptions are incorporated by reference and form part of the disclosure.

If the sulfonamide derivatives of general formula (I) are obtained in the form of a mixture of stereoisomers, preferably enantiomers or diastereomers, said mixtures can be separated by means of standard processes known in the prior art, for example chromatographic methods or crystallization with chiral agents.

Another aspect of the present invention is a medicament comprising at least one indol-6-yl sulfonamide derivative of general formula (I), optionally in the form of one of its stereoisomers, preferably enantiomer or diastereomer, its racemate, or in form of a mixture of at least two of its stereoisomers, preferably enantiomers or diastereomers, in any mixing ratio, or a corresponding physiologically acceptable salt thereof or a corresponding solvate thereof, and optionally at least one or more pharmaceutically acceptable adjuvants. This medicament is suitable for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and multiple sclerosis, schizophrenia, psychosis or infantile hyperkinesia (ADHD, attention deficit/hyperactivity disorder), and other disorders mediated by the 5-$HT_6$ serotonin receptor in humans and/or in animals, preferably in mammals, more preferably in humans.

Another aspect of the present invention is a medicament comprising at least one indol-6-yl sulfonamide derivative of general formula (Ia), optionally in the form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, and optionally at least one or more pharmaceutically acceptable adjuvants.

This medicament is suitable for 5-$HT_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimers disease, Parkinson's disease, Huntington's disease and multiple sclerosis, schizophrenia, psychosis or infantile hyperkinesia (ADHD, attention deficit/hyperactivity disorder), more suitable for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome.

Another aspect of the present invention is a medicament comprising at least one indol-6-yl sulfonamide derivative of general formula (Ib), optionally in the form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, and optionally at least one or more pharmaceutically acceptable adjuvants.

This medicament is suitable for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and multiple sclerosis, schizophrenia, psychosis or infantile hyperkinesia (ADHD, attention deficit/hyperactivity disorder), more suitable for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and multiple sclerosis, schizophrenia, psychosis or infantile hyperkinesia (ADHD, attention deficit/hyperactivity disorder) in humans and/or in animals, preferably in mammals, more preferably in humans.

Another aspect of the present invention is a medicament comprising at least one indol-6-yl sulfonamide derivative of general formula (Ic), optionally in the form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, and optionally at least one or more pharmaceutically acceptable adjuvants.

This medicament is suitable for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and multiple sclerosis, schizophrenia, psychosis or infantile hyperkinesia (ADHD, attention deficit/hyperactivity disorder), in humans and/or in animals, preferably in mammals, more preferably in humans.

The medicament obtained according to the present invention is particularly suitable for the administration to mammals, including humans. The medicament can preferably be administered to all ages, namely children, adolescents and adults.

Another aspect of the present invention is the use of at least one sulfonamide derivative of general formula (I), optionally in the form of one of its stereoisomers, preferably enantiomers or diastereomers, its racemate, or in form of a mixture of at least two of its stereoisomers, preferably enantiomers or diastereomers, in any mixing ration, or a corresponding physiologically acceptable salt thereof or a corresponding solvate thereof for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and multiple sclerosis, schizophrenia, psychosis or infantile hyperkinesia (ADHD, attention deficit/hyperactivity disorder), and other disorders mediated by the 5-HT$_6$ serotonin receptor in humans and/or in animals, preferably in mammals, more preferably in humans.

Another aspect of the present invention Is the use of at least one sulfonamide derivative of the previous general formula (Ia), optionally in the form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and multiple sclerosis, schizophrenia, psychosis or infantile hyperkinesia (ADHD, attention deficit/hyperactivity disorder) in humans and/or in animals, preferably in mammals, more preferably in humans, preferably for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome.

Another aspect of the present invention is the use of at least one sulfonamide derivative of the previous general formula (Ib), optionally in the form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and multiple sclerosis, schizophrenia, psychosis or infantile hyperkinesia (ADHD, attention deficit/hyperactivity disorder), and other disorders mediated by the 5-HT$_6$ serotonin receptor in humans and/or in animals, preferably in mammals, more preferably in humans, preferably for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimer's disease, Parkinson's disease, Huntington's disease and multiple sclerosis, schizophrenia, psychosis or infantile hyperkinesia (ADHD, attention deficit/hyperactivity disorder) and other disorders mediated by the 5-HT$_6$ serotonin receptor in humans and/or in animals, preferably in mammals, more preferably in humans.

Another aspect of the present invention Is the use of at least one sulfonamide derivative of the previous general formula (Ic), optionally in the form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, for the manufacture of a medicament for 5-HT$_6$ receptor regulation, for the prophylaxis and/or treatment of a disorder or disease related to food intake, preferably for the regulation of appetite, for the maintenance, increase or reduction of body weight, for the prophylaxis and/or treatment of obesity, bulimia, anorexia, cachexia or type II diabetes (non insulin dependent diabetes mellitus), preferably type II diabetes caused by obesity, for the prophylaxis and/or treatment of gastrointestinal tract disorders, preferably irritable bowel syndrome, for cognitive enhancement, for the prophylaxis and/or treatment of disorders of the central nervous system, anxiety, panic disorders, depression, bipolar disorders, cognitive memory disorders, senile dementia processes, neurodegenerative disorders, preferably Alzheimers disease, Parkinson's disease, Huntington's disease and multiple sclerosis, schizophrenia, psychosis or infantile hyperkinesia (ADHD, attention deficit/hyperactivity disorder) and other disorders mediated by the 5-HT$_6$ serotonin receptor in humans and/or in animals, preferably in mammals, more preferably in humans.

The preparation of the corresponding pharmaceutical compositions as well as the formulated medicaments can be carried out by means of conventional methods known in the prior art, for example, based on the indices of "Pharmaceutics: The Science of Dosage Forms", Second Edition, Aulton, M. E. (ED. Churchill Livingstone, Edinburgh (2002)); "Encyclopedia of Pharmaceutical Technology", Second Edition, Swarbrick, J. and Boylan, J. C. (Eds.), Marcel Dekker, Inc. New York (2002); "Modern Pharmaceutics", Fourth Edition, Banker G. S. and Rhodes C. T. (Eds.) Marcel Dekker, Inc. New York (2002), and "The Theory and Practice of Industrial Pharmacy", Lachman L., Lieberman H. and Kanig J. (Eds.), Lea & Febiger, Philadelphia (1986). The respective literature descriptions are incorporated as a reference and are part of this disclosure.

The pharmaceutical compositions, as well as the formulated medicaments prepared according to the present invention, can, in addition to at least one sulfonamide derivative of general formula (I), optionally in the form of one of its stereoisomers, preferably enantiomers or diastereomers, its racemate, or in form of a mixture of at least two of its stereoisomers, preferably enantiomers or diastereomers, in any mixing ratio, or a corresponding physiologically acceptable salt thereof or a corresponding solvate thereof, comprise other conventional auxiliary substances known in the prior art, preferably excipients, fillers, solvents, diluents, dyes, coating agents, matrix forming agents and/or binders.

As the skilled persons in the art also knows, the choice of the auxiliary substances and the amounts thereof depend on the intended administration route, for example, rectal, intravenous, intraperitoneal, intramuscular, intranasal, oral, buccal or topical.

Medicaments suitable for oral administration are, for example, tablets, coated tablets, capsules or multiparticulates, preferably granules or pellets, optionally subjected to compression in tablets, filled in capsules or suspended in solutions, suspensions or suitable liquids.

Medicaments suitable for parenteral, topical or inhalatory administration may preferably be chosen from the group consisting of solutions, suspensions, quickly reconstitutable dry preparations and also sprays.

Medicaments suitable for oral or percutaneous use can release the sulfonamide compounds of general formula (I) in a sustained manner, the preparation of these sustained release medicaments generally being known in the prior art.

Suitable sustained release forms, as well as the materials and methods for the preparation thereof, are known in the prior art, for example from the indices of "Modified-Release Drug Delivery Technology", Rathbone, J. JI, Hadgraft, J. and Roberts, M. S. (Eds.), Marcel Dekker, Inc., New York (2002); "Handbook of Pharmaceutical Controlled Release Technology", Wise, D. L. (Ed.), Marcel Dekker, Inc. New York (2000); "Controlled Drug Delivery", Vol. I, Basic Concepts, Bruck, S. D. (Ed.), CRD Press, Inc., Boca Raton (1983), and by Takada, K. and Yoshikawa, H., "Oral Drug Delivery", Encyclopedia of Controlled Drug Delivery, Mathiowitz, E. (Ed.), John Wiley & Sons, Inc., New York (1999), Vol. 2, 728-742; Fix, J., "Oral drug delivery, small intestine and colon", Encyclopedia of Controlled Drug Delivery, Mathiowitz, E. (Ed.), John Wiley & Sons, Inc., New York (1999), Vol. 2, 698-728. The respective literature references are incorporated by reference and form part of the disclosure.

The medicament of the present invention may also have at least one enteric coating, which dissolves according to the pH. As a result of this coating, the medicament may pass through the stomach without dissolving, and the compounds of general formula I are only released in the intestinal tract. The enteric coating preferably dissolves at a pH of between 5 and 7.5. The materials and methods suitable for preparing enteric coatings are also known in the prior art.

Typically, the pharmaceutical compositions and the medicaments comprise from 1 to 60% by weight of one or more sulfonamide derivatives of general formula (I), and from 40 to 99% by weight of one or more excipients.

The medicament substance amount to be administered to the patient varies according to the patient's weight, the administration route, the indication and the severity of the disorder. Usually from 1 mg to 2 g of at least one sulfonamide derivative of general formula (I) are administered per patient per day. The total daily dose can be administered to the patient in one or more doses.

Pharmaceutical Methods:

Binding to the $5HT_6$ Serotonin Receptor

HEK-293 cell membranes expressing the recombinant human $5HT_6$ receptor were supplied by Receptor Biology. The receptor concentration in said membranes is 2.18 pmol/mg of protein and the protein concentration is 9.17 mg/ml. The experimental protocol follows the method of B. L. Roth et al. [B. L. Roth, S. C. Craigo, M. S. Choudhary, A. Uluer, F. J. Monsma, Y. Shen, H. Y. Meltzer, D. R. Sibley: Binding of Typical and Atypical Antipshychotic Agents to 5-Hydroxytryptamine-6 and Hydroxytryptamine-7 Receptors. *The Journal of Pharmacology and Experimental Therapeutics,* 1994, 268, 1403], with slight modifications. The commercial membrane is diluted (1:40 dilution) with the binding buffer: 50 mM Tris-HCl, 10 mM $MgCl_2$, 0.5 mM EDTA (pH 7.4). The radioligand used is $[^3H]$-LSD at a concentration of 2.7 nM, the final volume being 200 µl. Incubation begins by adding 100 µl of the membrane suspension (≈22.9 µg of membrane protein), and is prolonged for 60 minutes at a temperature of 37° C. Incubation ends by quick filtration in a Harvester Brandel Cell through fiberglass filters of the Schleicher & Schuell G F 3362 trademark, pretreated with a 0.5% polyethyleneimine solution. The filters are washed three times with three milliliters of 50 mM Tris HCl buffer, pH 7.4. The filters are transferred to vials and 5 ml of Ecoscint H. liquid scintillation cocktail are added to each vial. The vials are left to equilibrate for several hours prior to their counting in a 1414 Wallac Winspectral scintillation counter. The non-specific binding is determined in the presence of 100 µM of serotonin. The assays are carried out in triplicate. The inhibition constants ($K_i$, nM) are calculated by non-linear regression analysis using the EBDA/LIGAND program [Munson and Rodbard, *Analytical Biochemistry,* 1980, 107, 220].

The respective literature descriptions are incorporated by reference and form part of the disclosure.

Measurements of Food Ingestion (Behavioural Model)

Male W rats (200-270 g) from Harlan, S.A. are used. The animals are acclimatized to the housings during at least 5 days prior to being subjected to any treatment. During this period, the animals are housed (in groups of five) in translucent cages and have free access to water and food. The animals are housed in individual cages at least 24 hours prior to starting the treatment.

The acute effect of the sulfonamide derivatives of formula (I) used inventively on food ingestion in rats in fasting conditions is then determined as follows:

The rats are kept in fasting conditions for 23 hours in their individual cages. After this period, the rats are orally or intraperitoneally treated with a dose of a composition containing a sulfonamide derivative of general formula (I) or a corresponding composition (vehicle) without said sulfonamide derivative. Immediately after this, the rat is left with pre-weighed food and the accumulated food intake is measured after 1, 2, 4 and 6 hours.

This food ingestion measuring method is also described in publications of Kask et al., *European Journal of Pharmacology* 414 (2001), 215-224, and Turnbull et al., *Diabetes,* Vol. 51, August, 2002. The respective bibliographic descriptions are incorporated as a reference and they form part of the disclosure.

The preparation of new compounds according to the invention is indicated in the following examples. The affinity for the $5HT_6$ serotonin receptor, as well as the galenic formulas applicable to the compounds of the invention, is also described. The examples indicated below, given as an illustrative example, should in no way limit the scope of the invention.

EXAMPLES

Example 1

Preparation of N-[1-(2-Dimethylaminoethyl)-1H-indole-6-yl]-5-chloro-3-methyl-benzo[b]thiophene-2-sulfonamide 185.6 mg (0.66 mMol) of 5-chloro-3-methyl-benzo[b]thiophene-2-sulfonyl chloride were added to a solution of 122 mg (0.6 mMol) of 6-amino-1-(2-dimethylaminoethyl)-1H-indole in 2 ml of dimethylformamide and 116 mg of N-ethyldiisopropylamine. The reaction mixture was stirred at the room temperature for 20 hours. Then it was evaporated to dryness, slightly alkalinized with sodium bicarbonate solution and extracted with chloroform. The organic phase was repeatedly washed with water and saturated solution of sodium bicarbonate, it was separated and dried with anhydrous sodium sulfate. The organic solution was evaporated to dryness and the resulting solid was purified by chromatography, obtaining 180 mg (67%) of N-[1-(2-dimethylaminoethyl)-1H-indole-6-yl]-5-choloro-3-methyl-benzo[b]thiophene-2-sulfonamide as an amorphous solid.

Example 2

Preparation of N-[1-(2-Dimethylaminoethyl)-1H-indole-6-yl]-naphthalene-2-sulfonamide 187 mg (80%) of the mentioned compound were obtained from 122 mg (0.6 mMol) of 6-amino-1-(2-dimethylaminoethyl)-1H-indole and 150 mg (0.66 mMol) of 2-naphthalene-sulfonyl chloride, by means of the process described in the Example 1, as a solid.

Example 3

Preparation of N-[1-(2-Dimethylaminoethyl)-1H-indole-6-yl]-naphthalene-1-sulfonamide 157 mg (67%) of the mentioned compound were obtained from 122 mg (0.6 mMol) of 6-amino-1-(2-dimethylaminoethyl)-1H-indole and 150 mg (0.66 mMol) of 1-naphthalenesulfonyl chloride, by means of the process described in the Example 1, as a solid.

Example 4

Preparation of N-[1-(2-Dimethylaminoethyl)-1H-indole-6-yl]-6-chloroimidazo[2,1-b]thiazole-5-sulfonamide 170 mg (67%) of the mentioned compound were obtained from 122 mg (0.6 mMol) of 6-amino-1-(2-dimethylaminoethyl)-1H-indole and 170 mg (0.66 mMol) of 6-chloroimidazo[2,1-b]thiazole-5-sulfonyl chloride, by means of the process described in the Example 1, as a solid.

Example 5

Preparation of N-[1-(2-Dimethylaminoethyl)-1H-indole-6-yl]-4 phenylbenzenesulfonamide 184 mg (73%) of the mentioned compound were obtained from 122 mg (0.6 mMol) of 6-amino-1-(2-dimethylaminoethyl)-1H-indole and 167 mg (0.66 mMol) of 4-phenylbenzenesulfonyl chloride, by means of the process described in the Example 1, as a solid.

Example 6

Preparation of N-[1-(2-Dimethylaminoethyl)-1H-indole-6-yl]-2-(naphthalene-1-yl)-ethanesulfonamide 100 mg (40%) of the mentioned compound were obtained from 122 mg (0.6 mMol) of 6-amino-1-(2-dimethylaminoethyl)-1H-indole and 168 mg (0.66 mMol) of 2-(naphthalene-1-yl)-ethanesulfonyl chloride, by means of the process described in the Example 1, as a solid.

Example 7

Preparation of N-[1-(2-Dimethylaminoethyl)-1H-indole-6-yl]-4-phenoxybenzenesulfonamide 190 mg (73%) of the mentioned compound were obtained from 122 mg (0.6 mMol) of 6-amino-1-(2-dimethylaminoethyl)-1H-indole and 177 mg (0.66 mMol) of 4-phenoxybenzenesulfonyl chloride, by means of the process described in the Example 1, as a solid.

Example 8

Preparation of N-[1-(2-dimethylaminoethyl)-1H-indole-6-yl]-3,5-dichlorobenzenesulfonamide 100 mg (41%) of the mentioned compound were obtained from 122 mg (0.6 mMol) of 6-amino-1-(2-dimethylaminoethyl)-1H-indole and 162 mg (0.66 mMol) of 3,5-dichlorobenzenesulfonyl chloride, by means of the process described in Example 1, as a solid.

Example 9

Preparation of 5-Chloro-3-methyl-N-[1-[2-(pyrrolidin-1-yl)ethyl-1H-indol-6-yl]-benzo[b]thiophene-2-sulfonamide 165 mg (58%) of the mentioned compound were obtained from 137 mg (0.6 mMol) of 6-amino-1-(2-(pyrrolidin-1-yl)ethyl)-1H-indol and 186 mg (0.66 mMol) of 5-chloro-3-methyl-benzo[b]-thiophene-2-sulfonyl chloride by means of the process described in Example 1 as a solid.

Example 10

Preparation of N-(1-[2-(Pyrrolidin-1-yl)ethyl]-1H-indol-6-yl]-napthyl-2-sulfonamide 142 mg (57%) of the mentioned compound were obtained from 137 mg (0.6 mMol) of 6-amino-1-(2-(pyrrolidin-1-yl)ethyl)-1H-indol and 150 mg (0.66 mMol) naphthalenesulfonyl chloride by means of the process described in Example 1 as a solid.

Example 11

Preparation of N-[1-[2-Pyrrolidin-1-yl]ethyl]-1H-indol-6-yl]-naphthalene-1-sulfonamide 166 (66%) of the mentioned compound were obtained from 137 mg (0.6 mMol) of 6-amino-1-(2-(pyrrolidin-1-yl)ethyl)-1H-indol and 150 mg (0.66 mMol) naphthalenesulfonyl chloride by means of the process described in Example 1 as a solid.

Example 12

Preparation of 6-Chloro-N-[1-[2-(pyrrolidin-1-yl)ethyl]-1H-indol-6-yl]-imidazo[2,1-b]thiazole-5-sulfonamide 170 mg (59%) of the mentioned compound were obtained from 137 mg (0.6 mMol) of 6-amino-1-(2-(pyrrolidin-1-yl)ethyl)-1H-indol and 170 mg 6-chloro-imidazo[2,1-b]thiazole-5-sulfonyl chloride by means of the process described in Example 1 as a solid.

Example 13

Preparation of 4-Phenyl-N-(1-(2-(pyrrolidin-1-yl)ethyl)-1H-indol-6-yl)benzenesulfonamide 205 mg (77%) of the mentioned compound were obtained from 137 mg (0.6 mMol) of 6-amino-1-(2-(pyrrolidin-1-yl)ethyl)-1H-indol and 169 mg (0.66 mmol) of 4-phenylbenzenesulfonyl chloride by means of the process described in Example 1 as an oil.

Example 14

Preparation of 2-(Naphthyl-1-yl)-N-(1-(2-(pyrrolidin-1-yl)-ethansulfonamid 182 mg (68%) of the mentioned compound were obtained from 137 mg (0.6 mMol) of 6-amino-1-(2-(pyrrolidin-1-yl)ethyl)-1H-indol and 182 mg (0.66 mmol) of 2-naphthalene-ethansulfonyl chloride by means of the process described in Example 1 as a solid.

Example 15

Preparation of 4-Phenoxy-N-(1-(2-(pyrrolidin-1-yl)ethyl)-1H-indol-6-yl)-benzenesulfonamide 185 mg (67%) of the mentioned compound were obtained from 137 mg (0.6 mMol) of 6-amino-1-(2-(pyrrolidin-1-yl)ethyl)-1H-indol and 177 mg (0.66 mmol) of 4-phenoxybenzenesulfonyl chloride by means of the process described in Example 1 as a solid.

Example 16

Preparation of 3,5-Dichloro-N-(1-(2-(Pyrrolidin-1-yl)-1H-indol-6-yl)-benzenesulfonamide 122 mg (46%) of the mentioned compound were obtained from 137 mg (0.6 mMol) of 6-amino-1-(2-(pyrrolidin-1-yl)ethyl)-1H-indol and 162 mg (0.66 mmol) of 3,5-dichlorobenzenesulfonyl chloride by means of the process described in Example 1 as a solid.

The yields are indicative and no added effort was made to improve them.

The melting point and spectroscopic data for identifying some of the compounds of the present invention are indicated in the following table.

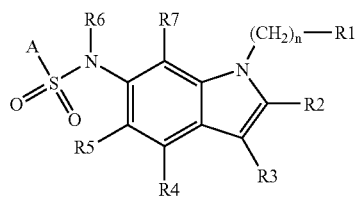

| Ex | R1 | R2 | R3 | R4 | R5 | R6 | R7 | n | A | m.p. °C | IR cm$^{-1}$ | $^1$H-NMR (300 MHz), δ (solvent) |
|---|---|---|---|---|---|---|---|---|---|---|---|---|
| 1 | (CH$_3$)$_2$N— | H | H | H | H | H | H | 2 | 5-chloro-2,3-dimethylbenzo[b]thiophene group | amorphous | 3422, 3247, 2943, 1467, 1340, 1158, 1114, 1080, 862, 651, 557. | 2.19(s, 9H); 2.55(t, 2H, J=6.7 Hz); 4.13(t, 2H, J=6.7 Hz); 6.42(d, 1H, 3.1 Hz); 6.69 (dd, 1H, J=8.3 Hz, J'=1.9 Hz); 7.13(d, 1H, 3.1 Hz); 7.23(m, 1H); 7.45-7.37(m, 2H); 7.63 (d, 1H, J=2.0 Hz); 7.69(d, 1H, J=8.6 Hz). (DMSO-d6) |
| 2 | (CH$_3$)$_2$N— | H | H | H | H | H | H | 2 | 6-methylnaphthalen-2-yl | 140-143 | 3422, 3246, 2935, 2760, 1468, 1336, 1159, 1132, 1074, 753, 711, 678, 553. | 2.19(s, 6H); 2.55(t, 2H, J=7.0 Hz); 4.11(t, 2H, J=7.0 Hz); 6.39(d, 1H, J=3.1 Hz); 6.67(dd, 1H, J=8.3 Hz, J'=1.4 Hz); 7.10(d, 1H, J=3.1 Hz); 7.19(s, 1H); 7.39 (d, 1H, J=8.4 Hz); 7.49-7.65 (m, 2H); 7.69(dd, 1H, J=8.9 Hz, J'=1.6 Hz); 7.81-7.88(m, 3H); 8.29(s, 1H).(DMSO-d6) |
| 3 | (CH$_3$)$_2$N— | H | H | H | H | H | H | 2 | 8-methylnaphthalen-1-yl | 139-142 | 3437, 2943, 1507, 1461, 1330, 1192, 1162, 1135, 961, 813, 763, 580, 472 | 2.21(s, 6H); 2.50(t, 2H, J=7.0 Hz); 4.03(t, 2H, J=7.0 Hz); 6.35 (d, 1H, J=3.1 Hz); 6.48(dd, 1H, J=8.4 Hz, J'=1.7 Hz); 7.00(s, 1H); 7.05(d, 1H, J=3.1 Hz); 7.29(m, 1H); 7.37(t, 1H, J=7.8 Hz); 7.60(m, 1H); 7.67(m, 1H); 7.92(d, 1H, J=8.1 Hz); 7.98(d, 1H, J=8.1 Hz); 8.10(d, 1H, J=7.3 Hz);8.73(d, 1H, J=8.8 Hz). (DMSO-d6) |
| 4 | (CH$_3$)$_2$N— | H | H | H | H | H | H | 2 | 6-chloro-5-methylimidazo[2,1-b]thiazol-yl | amorphous | 3448, 3110, 2814, 1459, 1325, 1250, 1178, 1141, 621. | 2.28(s, 6H); 2.61(t, 2H, J=7.0 Hz); 4.14(t, 2H, J=7.0 Hz); 6.41 (d, 1H, J=3.1 Hz); 6.81(m, 2H); 7.12(d, 1H, J=3.1 Hz); 7.19(m, 1H); 7.42(d, 1H, J=8.2 Hz); 7.56(d, 1H, J=4.6 Hz) (DMSO-d6) |
| 5 | (CH$_3$)$_2$N— | H | H | H | H | H | H | 2 | biphenyl-4-yl | amorphous | 3256, 2951, 2776, 1488, 1333, 1159, 1095, 763, 670, 591. | 2.24(s, 6H); 2.62(t, 2H, J=7.0 Hz); 4.15(t, 2H, J=7.0 Hz); 6.42 (d, 1H, J=3.1 Hz); 6.70(d, 1H, J=8.4 Hz); 7.12(d, 1H, J=3.1 Hz); 7.25(d, 1H, J=3.3 Hz); 7.34-7.48(m, 4H); 7.53(m, 2H); 7.59(AB sys, 2H, J=8.3 Hz); 7.78(AB sys, 2H, J=8.3 Hz). (DMSO-d6) |

-continued

| Ex | R1 | R2 | R3 | R4 | R5 | R6 | R7 | n | A | p.f. ° C. | IR | ¹H-RMN (300 MHz), δ (disolvente) |
|---|---|---|---|---|---|---|---|---|---|---|---|---|
| 6 | (CH₃)₂N— | H | H | H | H | H | H | 2 | 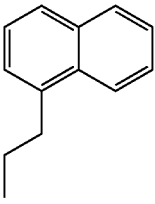 | amorphous | 3254, 2944, 1509, 1468, 1326, 1147, 970, 782, 716, 540. | 2.15(s, 6H); 2.62(t, 2H, J=7.1 Hz); 3.38(m, 2H); 3.49(m, 2H); 4.22(t, 2H, J=7.1 Hz); 6.47(d, 1H, J=2.8 Hz); 7.04(m, 2H); 7.23 (d, 1H, J=3.1 Hz); 7.26-7.45(m, 5H); 7.56(d, 1H, J=8.4 Hz); 7.68 (dd, 1H, J=7.5 Hz, J'=7.5 Hz); 7.77(d, 1H, J=8.3 Hz). (DMSO-d6) |
| 7 | (CH₃)₂N— | H | H | H | H | H | H | 2 | 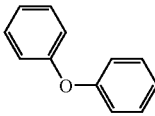 | amorphous | 3255, 2935, 2768, 1583, 1488, 1334, 1245, 1154, 1093, 694, 570, 539. | 2.28(s, 6H); 2.65(t, 2H, J=7.0 Hz); 4.16(t, 2H, J=7.0 Hz); 6.42 (d, 1H, J=3.0 Hz); 6.65(dd, 1H, J=8.4 Hz, J'=1.7 Hz); 6.90(AB sys, 2H, J=8.8 Hz); 7.00(AB sys, 2H, J=7.9 Hz); 7.13(d, 1H, J=3.1 Hz); 7.19(m, 1H); 7.24(m, 1H); 7.37(m, 2H); 7.43(d, 1H, J=8.3 Hz); 7.65(AB sys, 2H, J=8.9 Hz). (DMSO-d6) |
| 8 | (CH₃)₂N— | H | H | H | H | H | H | 2 | 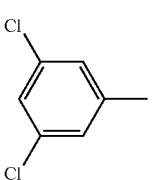 | 150-159 | 3437, 3072, 2920, 1568, 1471, 1346, 1303, 1171, 1140, 799, 670, 598. | 2.29(s, 6H); 2.66(t, 2H, J=6.8 Hz); 4.18(t, 2H, J=6.8 Hz); 6.45 (d, 1H); 6.67(d, 1H, J=8.4 Hz); 7.15(m, 1H); 7.19(m, 1H); 7.46 (m, 2H); 7.59(m, 2H). (DMSO-d6) |

| Ex | R1 | R2 | R3 | R4 | R5 | R6 | R7 | n | A | p.f. ° C. | ¹H-RMN (300 MHz), δ (disolvente) |
|---|---|---|---|---|---|---|---|---|---|---|---|
| 9 |  | H | H | H | H | H | H | 2 | 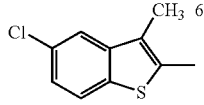 | 69-71 | 1.58(m, 4H); 2.31(m, 4H); 2.36(s, 3H); 2.59(m, 2H); 4.11(m, 2H); 6.31(s, 1H); 6.79(d, 1H, J=8.4 Hz); 7.09(s, 1H); 7.29(d, 1H, J=2.3 Hz); 7.38(d, 1H, J=8.5 Hz); 7.51(d, 1H, J=8.6 Hz); 7.94(d, 1H, J=1.0 Hz); 8.00(d, 1H, J=8.35 Hz); 10.39(b, 1H). (DMSO-d6) |
| 10 |  | H | H | H | H | H | H | 2 | 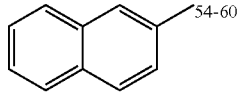 | 54-60 | 1.54(m, 4H); 2.24(m, 4H); 2.50(m, 2H); 4.06(m, 2H); 6.25(s, 1H); 6.77(d, 1H, J=8.4 Hz); 7.07(s, 1H); 7.23(m, 1H); 7.32(d, 1H, J=8.1 Hz); 7.61(m, 2H); 7.75(d, 1H, J=8.8 Hz); 7.95(d, 1H, J=7.6 Hz); 8.03(m, 2H); 8.34(s, 1H); 10.11(b, 1H). (DMSO-d6) |
| 11 |  | H | H | H | H | H | H | 2 | 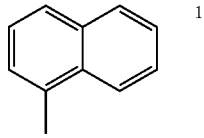 | 160-165 | 1.74(m, 4H); 2.71(m, 4H); 2.94(m, 2H); 4.24(m, 2H); 6.27(d, 1H, J=2.8 Hz); 6.61(d, 1H, J=8.6 Hz); 7.09(s, 1H); 7.24(d, 1H, J=8.5 Hz); 7.28(d, 1H, J=2.8 Hz); 7.54(t, 1H, J=7.9 Hz); 7.63(m, 1H); 7.71(m, 1H); 8.03(d, 1H, K=7.6 Hz); 8.11-8.23(m, 2H); 8.77(d, 1H, J=8.2 Hz); 10.46(b, 1H). (DMSO-d6) |
| 12 |  | H | H | H | H | H | H | 2 | 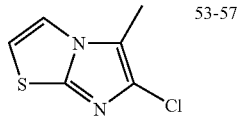 | 53-57 | 1.64(m, 4H); 2.50(m, 4H); 2.70(m, 2H); 4.14(m, 2H); 6.31(d, 1H, J=2.8 Hz); 6.71(d, 1H, J=8.8 Hz); 7.11(s, 1H); 7.31(d, 1H, J=8.6 Hz); 7.37(d, 1H, J=2.9 Hz); 7.56(d, 1H, J=4.4 Hz); 7.91(d, 1H, J=4.5 Hz); 10.63(b, 1H). (DMSO-d6) |
| 13 |  | H | H | H | H | H | H | 2 | 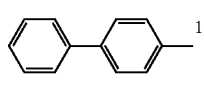 | 178-181 | 1.55(m, 4H); 2.33(m, 4H); 2.61(m, 2H); 4.11(m, 2H); 6.30(d, 1H, J=2.8 Hz); 6.79(dd, 1H, J=8.2, J'=1.6 Hz); 7.09(s, 1H); 7.28(d, 1H, J=2.8 Hz); 7.34-7.49(m, 4H); 7.67(d, 2H, J=7.0 Hz); 7.76(AB sys, 2H, J=8.7 Hz); 7.80(AB sys, 2H, J=8.7 Hz); 10.05(bs, 1H). (DMSO-d6) |

-continued

| | | | | | | | | | | |
|---|---|---|---|---|---|---|---|---|---|---|
| 14 | pyrrolidine-N | H | H | H | H | H | 2 | naphthyl-propyl | oil | 1.49(m, 4H); 2.31(m, 4H); 2.66(t, 2H, J=6.5 Hz); 3.3(m, 4H); 4.16(t, 2H, J=6.5 Hz); dd, 1H, J=8.4, J'=1.8 Hz); 7.13(m, 1H); 7.33-7.44(m, 5H); 7.48(d, 1H, J=8.6 Hz); 7.52(d, 1H, J=8.4 Hz); 7.75(t, 1H, J=4.8 Hz); 7.85(d, 1H, J=8.1 Hz); 9.84(s, 1H). (DMSO-d6) |
| 15 | pyrrolidine-N | H | H | H | H | H | 2 | phenoxy-phenyl | 59-62 | 1.61(m, 4H); 2.41(m, 4H); 2.66(t, 2H, J=6.5 Hz); 4.12(t, 2H, J=6.5 Hz); 6.30(d, 1H, J=2.8 Hz); 6.75(dd, 1H, J=8.4, J'=1.4 Hz); 6.99(d, 2H, J=8.8 Hz); 7.04(d, 2H, J=7.9 Hz); 7.10(s, 1H); 7.21(t, 1H, J=7.4 Hz); 7.29(d, 1H, J=3.1 Hz); 7.36(d, 1H, J=8.5 Hz); 7.41(t, 2H, J=7.9 Hz); 7.69(d, 2H, J=8.8 Hz); 9.98(bs, 1H). (DMSO-d6) |
| 16 | pyrrolidine-N | H | H | H | H | H | 2 | 3,5-dichlorophenyl | 145-157 | 1.62(m, 4H); 2.39(m, 4H); 2.64(t, 2H, J=6.7 Hz); 4.15(t, 2H, J=6.7 hz); 6.32(d, 1H, J=3.1 Hz); 6.73(dd, 1H, J=8.4, J'=1.8 Hz); 7.10(s, 1H); 7.33(d, 1H, J=3.2 Hz); 7.40(d, 1H, J=8.5 Hz); 7.63(d, 2H, J=1.9 Hz); 7.90(t, 1H, J=1.9 Hz); 10.20(bs, 1H). (DMSO-d6) |

Pharmaceutical Particulars:

Binding of the new compounds of general formula (I) to the 5-$HT_6$ receptor was determined as previously described.

The binding results for some of the compounds of the present invention are indicated in the following table:

TABLE

| Example | % Inhibition $10^{-6}$M | $K_i$ (nM) |
|---|---|---|
| 1 | 98.6 | 90.2 |
| 2 | 97.7 | 41.2 |
| 3 | 95.3 | 19.8 |
| 4 | 90.8 | 55.2 |
| 5 | 93.4 | 129.4 |
| 6 | 94.5 | 74.5 |
| 7 | 95.1 | 118.6 |
| 8 | 86.9 | 159.1 |

The daily posology in human medicine is comprised between 1 milligram and 2 grams of medicinal product which can be administered in one or several doses. The compositions are prepared in forms that are compatible with the administration route used, preferably tablets, coated tablets, capsules, suppositories, solutions or suspensions. These compositions are prepared by means of known methods and comprise from 1 to 60% by weight of the medicament substance (compound of general formula I), and 40 to 99% by weight of the suitable pharmaceutical vehicle compatible with the medicament substance and the physical form of the composition used. The formula of a tablet containing a product of the invention is provided by way of example.

Example of formula per tablet:

| | |
|---|---|
| Example 1 | 5 mg |
| Lactose | 60 mg |
| Crystalline cellulose | 25 mg |
| Povidone K 90 | 5 mg |
| Pregelatinized starch | 3 mg |
| Colloidal silicon dioxide | 1 mg |
| Magnesium stearate | 1 mg |
| Total weight per tablet | 100 mg |

The invention claimed is:

1. A sulfonamide compound of general formula (Ia),

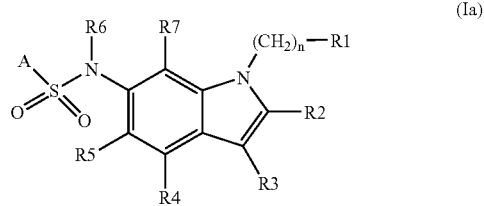

wherein $R^1$ represents a —$NR^8R^9$ radical or a saturated or unsaturated, optionally at least mono-substituted, optionally at least one heteroatom as a ring member containing cycloaliphatic radical, which may be condensed with a saturated or unsaturated, optionally at least mono-substituted, optionally at least one heteroatom as a ring member containing mono- or bicyclic cycloaliphatic ring system, $R^2$, $R^3$, $R^4$, $R^5$ and $R^7$, identical or different, each represent hydrogen, halogen, nitro, alkoxy, cyano, a saturated or unsaturated, linear or branched, optionally at least mono-substituted aliphatic radical, or an optionally at least mono-substituted phenyl radical or an optionally at least mono-substituted heteroaryl radical, $R^6$ represents hydrogen or a saturated or unsaturated, linear or branched, optionally at least mono-substituted aliphatic radical, $R^8$ and $R^9$, identical or different, each represent hydrogen or a saturated or unsaturated, linear or branched, optionally at least mono-substituted aliphatic radical, with the proviso that $R^8$ and $R^9$ are not hydrogen at the same time, and if one of them, $R^8$ or $R^9$, is a saturated or unsaturated, linear or branched, optionally at least mono-substituted $C_1$-$C_4$ aliphatic radical, the other one is a saturated or unsaturated, linear or branched, optionally at least mono-substituted aliphatic radical with at least five carbon atoms, or R⁸ and R⁹, together with the bridging nitrogen atom, form a saturated or unsaturated, optionally at least mono-substituted heterocyclic ring, which may contain at least one further heteroatom as a ring member and/or which may be condensed with a saturated or unsaturated, optionally at least mono-substituted, optionally at least one heteroatom as a ring member containing mono- or bicyclic cycloaliphatic ring system, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings and n is 0, 1, 2, 3 or 4;

optionally in form of one of its stereoisomers, a racemate or in form of a mixture of at least two of its stereoisomers, in any mixing ratio, or a salt thereof.

2. A compound according to claim 1, wherein $R^1$ represents a —$NR^8R^9$ radical or a saturated or unsaturated, optionally at least mono-substituted, optionally at least heteroatom as a ring member containing 5- or 6-membered cycloaliphatic radical, which may be condensed with a saturated or unsaturated, optionally at least mono-substituted, optionally at least one heteroatom as a ring member containing mono- or bicyclic cycloaliphatic ring system, whereby the rings of the ring system are 5- or 6-membered.

3. A compound according to claim 1, wherein $R^2$, $R^3$, $R^4$, $R^5$ and $R^7$, identical or different, each represent hydrogen, a linear or branched, optionally at least mono-substituted $C_1$-$C_6$ alkyl radical, a linear or branched, optionally at least mono-substituted $C_2$-$C_6$ alkenyl radical, or a linear or branched, optionally at least mono-substituted $C_2$-$C_6$ alkynyl radical.

4. A compound according to claim 1, wherein $R^6$ represents hydrogen, a linear or branched, optionally at least mono-substituted $C_1$-$C_6$ alkyl radical, a linear or branched, optionally at least mono-substituted $C_2$-$C_6$ alkenyl radical, a linear or branched, optionally at least mono-substituted $C_2$-$C_6$ alkynyl radical.

5. A compound according to claim 1, wherein $R^8$ and $R^9$, identical or different, each represent hydrogen, a linear or branched, optionally at least mono-substituted $C_1$-$C_{10}$ alkyl radical, a linear or branched, optionally at least mono-substituted $C_2$-$C_{10}$ alkenyl radical, a linear or branched, optionally at least mono-substituted $C_2$-$C_{10}$ alkynyl radical, or R⁸ and R⁹, together with the bridging nitrogen form a saturated or unsaturated, optionally at least mono-substituted, optionally at least one further heteroatom as a ring member containing 5- or 6-membered heterocyclic ring, which may be condensed with a saturated or unsaturated, optionally at least mono-substituted, optionally at least one heteroatom as a ring member containing mono- or bicyclic cycloaliphatic ring system, whereby the rings of the ring system are 5- 6- or 7-membered.

6. A compound according to claim 5, wherein $R^8$ and $R^9$, identical or different, each represent hydrogen or a linear or branched $C_1$-$C_{10}$ alkyl radical, or R⁸ and R⁹, together with the bridging nitrogen form a radical chosen from the group consisting of

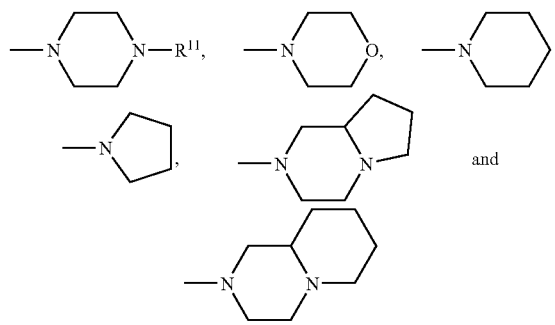

wherein $R^{11}$ represents hydrogen, a linear or branched $C_1$-$C_6$ alkyl radical or a benzyl radical.

7. A compound according to claim 1, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member.

8. A compound according to claim 1, selected from the group consisting of

[9] 5-Chloro-3-methyl-N-[1-[2-(pyrrolidin-1-yl)ethyl-1H-indol-6-yl]-benzo[b]thiophene-2-sulfonamide,

[10] N-(1-[2-(Pyrrolidin-1-yl)ethyl]-1H-indol-6-yl]-napthalene-2-sulfonamide,

[11] N-[1-[2-Pyrrolidin-1-yl]ethyl]-1H-indol-6-yl]-naphthalene-1-sulfonamide,

[12] 6-Chloro-N-[1-[2-(pyrrolidin-1-yl)ethyl]-1H-indol-6-yl]-imidazo[2,1-b]thiazole-5-sulfonamide,

[13] 4-Phenyl-N-(1-(2-pyrrolidin-1-yl)ethyl)-1H-indol-6-yl)-benzenesulfonamide

[14] 2-(Naphthyl-1-yl)-N-(1-(2-(pyrrolidin-1-yl)ethyl)-1H-indol-6-yl)-ethansulfonamide,

[15] 4-Phenoxy-N-(1-(2-(pyrrolidin-1-yl)ethyl)-1H-indol-6-yl)-benzenesulfonamide and

[16] 3,5-Dichloro-N-(1-(2-(pyrrolidin-1-yl)-1H-indol-6-yl)-benzenesulfonamide, and their corresponding salts.

9. A sulfonamide compound of general formula (Ib)

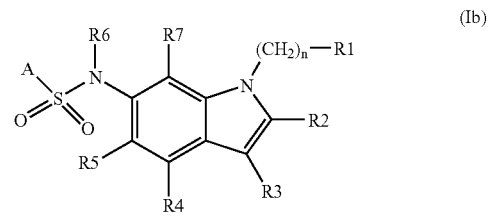

(Ib)

wherein $R^1$ is a —$NR^8R^9$ radical, $R^2$, $R^3$, $R^4$, $R^5$ and $R^7$, identical or different, each represent hydrogen, halogen, nitro, alkoxy, cyano, a saturated or unsaturated, linear or branched, optionally at least mono-substituted aliphatic radical, or an optionally at least mono-substituted phenyl or optionally at least mono-substituted heteroaryl radical, $R^6$ represents hydrogen or a saturated or unsaturated, linear or branched, optionally at least mono-substituted aliphatic radical, $R^8$ and $R^9$, identical or different, each represent hydrogen or a saturated or unsaturated, linear or branched, optionally at least mono-substituted $C_1$-$C_4$ aliphatic radical, A represents an optionally at least mono-substituted mono- or polycyclic aromatic ring system, which may be bonded via an optionally at least mono-substituted alkylene, alkenylene or alkynylene group and/or which may contain at least one heteroatom as a ring member in one or more of its rings and n is 0, 1, 2, 3 or 4 optionally in form of one of its stereoisomers, a racemate or in form of a mixture of at least two of its stereoisomers, in any mixing ratio, or a salt thereof.

10. A compound according to claim 9, wherein $R^2$, $R^3$, $R^4$, $R^5$ and $R^7$, identical or different, each represent hydrogen, a linear or branched, optionally at least mono-substituted $C_1$-$C_6$ alkyl radical, a linear or branched, optionally at least mono-substituted $C_2$-$C_6$ alkenyl radical, or a linear or branched, optionally at least mono-substituted $C_2$-$C_6$ alkynyl radical.

11. A compound according to claim 9, wherein $R^6$ represents hydrogen, a linear or branched, optionally at least mono-substituted $C_1$-$C_6$ alkyl radical, a linear or branched, optionally at least mono-substituted $C_2$-$C_6$ alkenyl radical, a linear or branched, optionally at least mono-substituted $C_2$-$C_6$ alkynyl radical.

12. A compound according to claim 9, wherein $R^8$ and $R^9$, identical or different, each represent hydrogen or a linear or branched, optionally at least mono-substituted $C_1$-$C_4$ alkyl radical, with the proviso that $R^8$ and $R^9$ are not hydrogen at the same time.

13. A compound according to claim 9, wherein A represents an optionally at least mono-substituted mono- or polycyclic aromatic ring system, wherein the ring(s) is/are 5- or 6-membered, which may be bonded via an optionally at least mono-substituted $C_1$-$C_6$ alkylene group, an optionally at least mono-substituted $C_2$-$C_6$ alkenylene group or an optionally at least mono-substituted $C_2$-$C_6$ alkynylene group and/or wherein the ring(s) may contain at least one heteroatom as a ring member.

14. A compound according to claim 9, selected from the group consisting of

[1] N-[1-(2-Dimethylaminoethyl)-1H-indol-6-yl]-5-chloro-3-methylbenzo[b]thiophene-2-sulfonamide,

[2] N-[1-(2-Dimethylaminoethyl)-1H-indol-6-yl]-naphthalene-2-sulfonamide,

[3] N-[1-(2-Dimethylaminoethyl)-1H-indol-6-yl]-naphthalene-1-sulfonamide,

[4] N-[1-(2-Dimethylaminoethyl)-1H-indol-6-yl]-6-chloroimidazo[2,1-b]thiazole-5-sulfonamide,

[5] N-[1-(2-Dimethylaminoethyl)-1H-indol-6-yl]-4-phenylbenzenesulfonamide,

[6] N-[1-(2-Dimethylaminoethyl)-1H-indol-6-yl]-2-(naphthalene-1-yl)-ethanesulfonamide,

[7] N-[1-(2-Dimethylaminoethyl)-1H-indol-6-yl]-4-phenoxybenzenesulfonamide,

[8] N-[1-(2-Dimethylaminoethyl)-1H-indol-6-yl]-3,5-dichlorobenzenesulfonamide, and their corresponding salts.

15. A process for obtaining a sulfonamide derivative of general formula (Ia), according to claim 1, wherein at least one compound of general formula (II), or one of its suitably protected derivatives,

wherein X is an acceptable leaving group; is reacted with at least one 6-aminoindole of general formula (III), or one of its suitably protected derivatives;

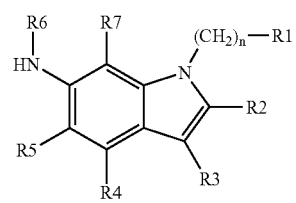

to yield the corresponding sulfonamide and optionally, from the latter, the protective groups can be removed if necessary.

16. A process for obtaining a sulfonamide derivative of general formula (Ia), according to claim 1, wherein $R^6$ is $C_1$-$C_6$ alkyl, comprising reacting at least one compound of general formula (Ia) wherein $R^6$ is an hydrogen atom, with an alkyl halogenide or dialkyl sulfate.

17. A process for preparing a salt of general formula (Ia), according to claim 1, wherein at least one compound of the general formula (Ia) is reacted with a mineral acid or an organic acid in a suitable solvent.

18. A pharmaceutical composition comprising a therapeutically effective amount of at least one compound according to claim 1 and optionally one or more pharmacologically acceptable excipients.

19. A pharmaceutical composition comprising a therapeutically effective amount of at least one compound according to claim 9 and optionally one or more pharmacologically acceptable excipients.

20. A compound according to claim 1, wherein the compound is in the form of a physiologically acceptable salt thereof.

21. A compound according to claim 1, wherein the compound is in the form of its enantiomers or diastereomers, or in the form of a mixture of at least two of its enantiomers and/or diastereomers.

22. A compound according to claim 2, wherein $R^1$ represents an —$NR^8R^9$ radical or a radical selected from the group consisting of

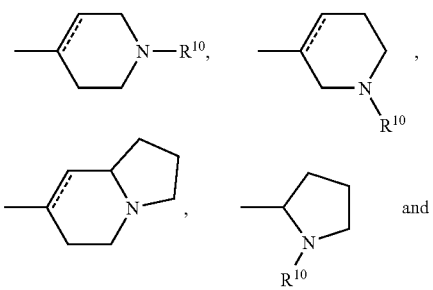

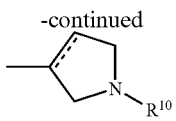

wherein, if present, the dotted line represents an optional chemical bond, and $R^{10}$ represents hydrogen, a linear or branched $C_1$-$C_6$ alkyl radical or a benzyl radical.

23. A compound according to claim 22, wherein the radical contains $R^{10}$, which is hydrogen or a $C_1$-$C_2$ alkyl radical.

24. A compound according to claim 3, wherein $R^2$, $R^3$, $R^4$, $R^5$ and $R^7$, identical or different, each represent hydrogen or a linear or branched, optionally at least mono-substituted $C_1$-$C_6$ alkyl radical.

25. A compound according to claim 24, wherein $R^2$, $R^3$, $R^4$, $R^5$ and $R^7$ each represent hydrogen.

26. A compound according to claim 4, wherein $R^6$ represents hydrogen or a linear or branched, optionally at least mono-substituted $C_1$-$C_6$ alkyl radical.

27. A compound according to claim 26, wherein $R^6$ represents hydrogen or a $C_1$-$C_2$ alkyl radical.

28. A compound according to claim 6, wherein $R^{11}$ represents hydrogen or a $C_1$-$C_2$ alkyl radical.

29. A compound according to claim 7, wherein A represents an optionally at least mono-substituted mono- or polycyclic aromatic ring system, wherein the ring(s) is/are 5- or 6-membered and wherein one or more of the rings contain at least one heteroatom.

30. A compound according to claim 7, wherein A is a radical selected from the group consisting of

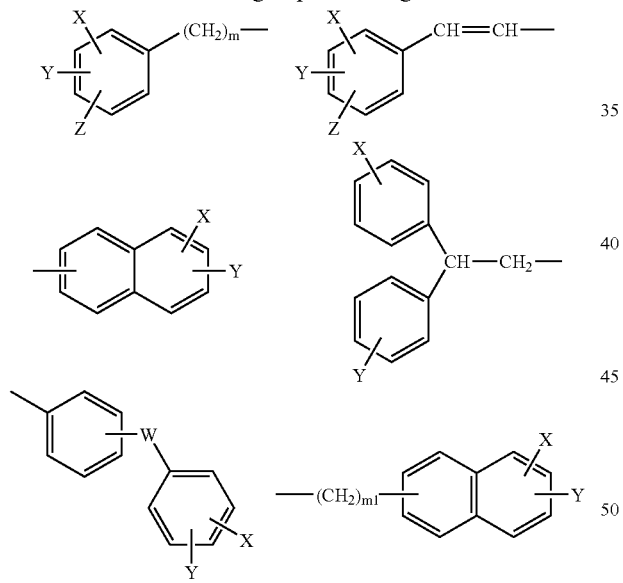

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2.

31. A compound according to claim 9, wherein the compound is in the form of a physiologically acceptable salt thereof.

32. A compound according to claim 9, wherein the compound is in the form of its enantiomers or diastereomers, or in the form of a mixture of at least two of its enantiomers and/or diastereomers.

33. A compound according to claim 10, wherein $R^2$, $R^3$, $R^4$, $R^5$ and $R^7$, identical or different, each represent hydrogen or a linear or branched, optionally at least mono-substituted $C_1$-$C_6$ alkyl radical.

34. A compound according to claim 33, wherein $R^2$, $R^3$, $R^4$, $R^5$ and $R^7$ each represent hydrogen.

35. A compound according to claim 11, wherein $R^6$ represents hydrogen or a linear or branched, optionally at least mono-substituted $C_1$-$C_6$ alkyl radical.

36. A compound according to claim 35, wherein $R^6$ represents hydrogen or a $C_1$-$C_2$ alkyl radical.

37. A compound according to claim 12, wherein $R^8$ and $R^9$, identical or different, each represent hydrogen or a $C_1$-$C_2$ alkyl radical.

38. A compound according to claim 13, wherein A represents an optionally at least mono-substituted mono- or polycyclic aromatic ring system, wherein the ring(s) is/are 5- or 6-membered and wherein one or more of the rings contain at least one heteroatom.

39. A compound according to claim 13, wherein A is a radical selected from the group consisting of

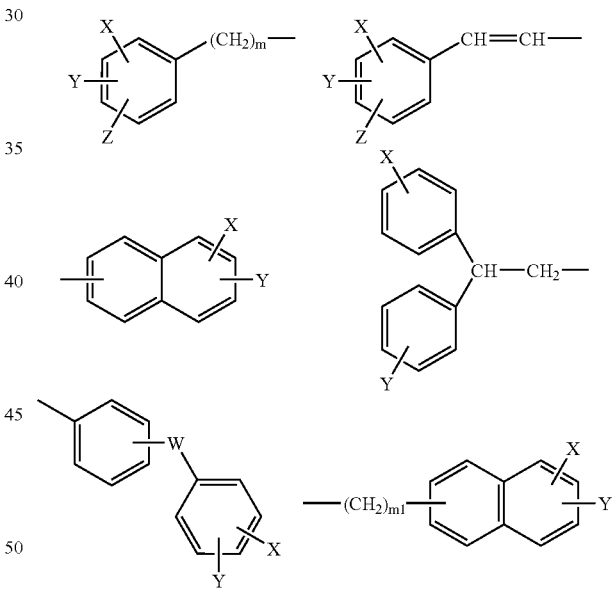

wherein X, Y, Z, independently from one another, each represent a radical selected from the group consisting of hydrogen, fluorine, chlorine, bromine, linear or branched $C_1$-$C_6$ alkyl, linear or branched $C_1$-$C_6$ alkoxy, linear or branched $C_1$-$C_6$ alkylthio, a trifluoromethyl radical, a cyano radical and a —$NR^{12}R^{13}$ radical, wherein $R^{12}$ and $R^{13}$, identical or different, each represent hydrogen or linear or branched $C_1$-$C_6$ alkyl, W represents a single chemical bond between the two rings, a $CH_2$, O, S group or a $NR^{14}$ radical, wherein $R^{14}$ is hydrogen or a linear or branched $C_1$-$C_6$ alkyl, m is 0, 1, 2, 3 or 4 and m1 is 1 or 2.

40. A process for obtaining a sulfonamide derivative of general formula (Ib) according to claim 9, wherein at least one compound of general formula (II), or one of its suitably protected derivatives,

(II)

wherein X is an acceptable leaving group is reacted with at least one 6-aminoindole of general formula (III), or one of its suitably protected derivatives;

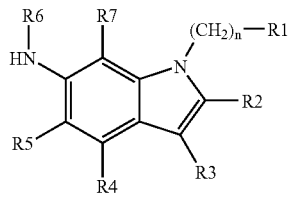
(III)

to yield the corresponding sulfonamide and optionally, from the latter, the protective groups can be removed if necessary.

41. A process for obtaining a sulfonamide derivative of general formula (Ib) according to claim 9, wherein $R^6$ is $C_1$-$C_6$ alkyl, comprising reacting at least one compound of general formula (Ib) wherein $R^6$ is an hydrogen atom, with an alkyl halogenide or dialkyl sulfate.

42. A process for preparing a salt of general formula (Ib) according to claim 9, wherein at least one compound of the general formula (Ib) is reacted with a mineral acid or an organic acid in a suitable solvent.

43. A process according to claim 15, wherein X is an halogen atom.

44. A process according to claim 15, wherein X is chlorine.

45. A process according to claim 40, wherein X is an halogen atom.

46. A process according to claim 40, wherein X is chlorine.

* * * * *